US010287561B2

(12) United States Patent
Alvarez et al.

(10) Patent No.: US 10,287,561 B2
(45) Date of Patent: May 14, 2019

(54) POLYPEPTIDE HAVING A POLYESTER DEGRADING ACTIVITY AND USES THEREOF

(71) Applicants: CARBIOS, Saint-Beauzire (FR); INSTITUT NATIONAL DE LA RECHERCHE AGRONOMIQUE, Paris (FR); INSTITUT NATIONAL DES SCIENCES APPLIQUEES, Toulouse (FR); CENTRE NATIONAL DE LA RECHERCHE SCIENTIFIQUE, Paris (FR)

(72) Inventors: Pablo Alvarez, Arc-sur-Tille (FR); Emilie Amillastre, Toulouse (FR); Sophie Duquesne, Toulouse (FR); Alain Marty, Toulouse (FR)

(73) Assignees: CARBIOS, Saint-Beauzire (FR); INSTITUT NATIONAL DE LA RECHERCHE AGRONOMIQUE, Paris (FR); INSTITUE NATIONAL DES SCIENCES APPLIQUEES, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 35 days.

(21) Appl. No.: 15/520,431

(22) PCT Filed: Oct. 20, 2015

(86) PCT No.: PCT/EP2015/074222
§ 371 (c)(1),
(2) Date: Apr. 20, 2017

(87) PCT Pub. No.: WO2016/062695
PCT Pub. Date: Apr. 28, 2016

(65) Prior Publication Data
US 2017/0313998 A1  Nov. 2, 2017

(30) Foreign Application Priority Data

Oct. 21, 2014 (EP) ..................................... 14306672

(51) Int. Cl.
*C12N 1/20* (2006.01)
*C12N 9/18* (2006.01)
*C08J 11/10* (2006.01)
*C12N 9/16* (2006.01)
*C12P 7/56* (2006.01)

(52) U.S. Cl.
CPC .............. *C12N 9/18* (2013.01); *C08J 11/105* (2013.01); *C12N 9/16* (2013.01); *C12P 7/56* (2013.01); *C07K 2319/02* (2013.01); *C07K 2319/21* (2013.01); *C07K 2319/24* (2013.01); *C08J 2367/04* (2013.01)

(58) Field of Classification Search
CPC ........................................................ C12N 1/20
See application file for complete search history.

(56) References Cited

U.S. PATENT DOCUMENTS

| 5,032,512 | A | 7/1991 | Witholt et al. |
|---|---|---|---|
| 5,145,779 | A | 9/1992 | Pometto et al. |
| 5,212,219 | A | 5/1993 | Griffin |
| 5,316,847 | A | 5/1994 | Suominen |
| 5,378,738 | A | 1/1995 | Deguchi et al. |
| 5,426,047 | A | 6/1995 | Ito et al. |
| 6,312,578 | B1 | 11/2001 | Canivenc et al. |
| 6,429,006 | B1 | 8/2002 | Porro et al. |
| 7,465,575 | B2 | 12/2008 | Nilsson |
| 7,534,597 | B2 | 5/2009 | Hause et al. |
| 7,960,154 | B1 | 6/2011 | Nakajima et al. |
| 8,137,953 | B2 | 3/2012 | Miller et al. |
| 8,476,056 | B2 | 7/2013 | Hoang et al. |
| 8,614,076 | B2 | 12/2013 | Wada et al. |
| 8,859,260 | B2 | 10/2014 | Sawai et al. |
| 9,476,073 | B2 | 10/2016 | Boisart |
| 9,528,132 | B2 | 12/2016 | Mazzoli et al. |
| 10,124,512 | B2 | 11/2018 | Boisart et al. |
| 2005/0261465 | A1 | 11/2005 | Nagarajan |
| 2006/0106120 | A1 | 5/2006 | Abe et al. |
| 2011/0008855 | A1 | 1/2011 | Park et al. |
| 2011/0200771 | A1 | 8/2011 | Barclay |
| 2011/0245057 | A1 | 10/2011 | Scoledes et al. |
| 2011/0319588 | A1 | 12/2011 | Coupin et al. |

(Continued)

FOREIGN PATENT DOCUMENTS

| CN | 101 457 218 | 6/2009 |
|---|---|---|
| CN | 102675712 | 9/2012 |

(Continued)

OTHER PUBLICATIONS

Niaounakis, 2013. Chapter 4: Disposal. Biopolymers Reuse, Recycling, and Disposal. A Volume in Plastics Design Library, a PDL Handbook Series. ISBN 978-1-4557-3145-9, published by Elsevier Inc.*

(Continued)

*Primary Examiner* — Karen Cochrane Carlson
(74) *Attorney, Agent, or Firm* — Saliwanchik, Lloyd & Eisenschenk

(57) ABSTRACT

The present invention relates to a new isolated polypeptide comprising an amino acid sequence having at least 94%, 95%, 99% or 100% identity to the full length amino acid sequence set forth in SEQ ID NO: 1, and having a polyester degrading activity, and uses thereof.

Figure 1:
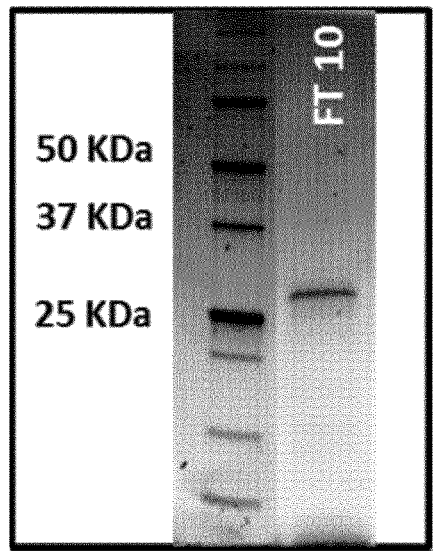

12 Claims, 4 Drawing Sheets
Specification includes a Sequence Listing.

(56) References Cited

U.S. PATENT DOCUMENTS

| | | |
|---|---|---|
| 2012/0184005 A1 | 7/2012 | Ferreira et al. |
| 2013/0274373 A1 | 10/2013 | Yoshikawa et al. |
| 2014/0303278 A1 | 10/2014 | Ferreira et al. |
| 2015/0056673 A1 | 2/2015 | Boisart |
| 2015/0290840 A1 | 10/2015 | Boisart et al. |
| 2016/0280881 A1 | 9/2016 | Boisart et al. |
| 2017/0114205 A1 | 4/2017 | Maille |
| 2017/0349723 A1 | 12/2017 | Ferreira et al. |
| 2018/0051264 A1 | 2/2018 | Li et al. |
| 2018/0142097 A1 | 5/2018 | Guemard et al. |
| 2018/0186943 A1 | 7/2018 | Chateau et al. |

FOREIGN PATENT DOCUMENTS

| | | |
|---|---|---|
| CN | 103980535 | 8/2014 |
| EP | 0 421 413 | 4/1991 |
| EP | 0 738 752 | 10/1996 |
| EP | 1 548 053 | 6/2005 |
| EP | 2 013 280 | 1/2009 |
| EP | 2 348 122 | 7/2011 |
| EP | 2 377 945 | 10/2011 |
| EP | 2 471 910 | 7/2012 |
| EP | 2 626 386 | 8/2013 |
| JP | 2000-506442 | 5/2000 |
| JP | 2002-293982 | 10/2002 |
| JP | 2002-320499 | 11/2002 |
| JP | 2002 362578 | 12/2002 |
| JP | 2003-079388 | 3/2003 |
| JP | 2003-128835 | 5/2003 |
| JP | 2004 058010 | 2/2004 |
| JP | 2004-290130 | 10/2004 |
| JP | 2004 292705 | 10/2004 |
| JP | 2007 319092 | 12/2007 |
| JP | 2012 149273 | 8/2012 |
| JP | 2012-152171 | 8/2012 |
| JP | 2013 000099 | 1/2013 |
| JP | 5 630597 | 11/2014 |
| KR | 20110045975 | 5/2011 |
| WO | WO 89/10381 | 11/1989 |
| WO | WO 2005/026245 | 3/2005 |
| WO | WO 2010/012805 | 2/2010 |
| WO | WO 2010/081887 | 7/2010 |
| WO | WO 2011/039489 | 4/2011 |
| WO | WO 2013/144239 | 10/2013 |
| WO | WO 2014/079844 | 5/2014 |
| WO | WO 2014/122698 | 8/2014 |
| WO | WO 2014/167518 | 10/2014 |
| WO | WO 2014/167562 | 10/2014 |
| WO | WO 2015/067619 | 5/2015 |
| WO | WO 2015/097104 | 7/2015 |
| WO | WO 2015/173265 | 11/2015 |
| WO | WO 2016/198650 | 12/2016 |
| WO | WO 2016/198652 | 12/2016 |
| WO | WO2017/108577 | 6/2017 |
| WO | WO2017/198786 | 11/2017 |

OTHER PUBLICATIONS

Sukkhum et al. 2009; A novel poly (L-lactide) degrading actinomycetes isolated from Thai forest soil, phylogenic relationship and enzyme characterization. J. Gen. Applied Microbiology. 55: 459-467.*

Sukkhum et al. 2012 (published online Nov. 2, 2011); Poly (L-lactide)-degrading enzyme production by Actinomadura keratinilytica T16-1 in 3 L airlift bioreactor and its degradation ability for biological recycle. J. Microbiol. Biotechnol. 22(1): 92-99.*

Sugimori. Mar. 2013. Protease, washing agent containing the protease, and method of manufacturing the washing agent. EMBL AB809463.*

Sukkhum, S. et al. "A novel poly ($_L$-lactide) degrading actinomycetes isolated from Thai forest soil, phylogenic relationship and the enzyme characterization" *The Journal of General and Applied Microbiology*, 2009, pp. 459-467, vol. 55, No. 6.

Sukkhum, S. et al. "Poly($_L$-Lactide)-Degrading Enzyme Production by *Actinomadura keratinilytica* T16-1 in 3 L Airlift Bioreactor and Its Degradation Ability for Biological Recycle" *Journal of Microbiology and Biotechnology*, Jan. 28, 2012, pp. 92-99, vol. 22, No. 1.

Written Opinion in International Application No. PCT/EP2015/074222, dated Feb. 1, 2016, pp. 1-5.

Matsuda, E. et al. "Gene Cloning and Molecular Characterization of an Extracellular Poly($_L$-Lactic Acid) Depolymerase from *Amycolatopsis* sp. Strain K104-1" *Journal of Bacteriology*, Nov. 2005, pp. 7333-7340, vol. 187, No. 21.

Database WPI, Accession No. 2009-K99963, Jun. 17, 2009, pp. 1-2, XP-002690934.

Database WPI, Accession No. 2008-F66138, Dec. 13, 2007, pp. 1-2, XP-002690935.

Wang, Z.-Y. et al. "Gene Cloning and Characterization of a Poly($_L$-Lactic Acid) Depolymerase from *Pseudomonas* sp. Strain DS04-T" *J Polym Environ*, Aug. 28, 2011, pp. 827-833, vol. 19, No. 4.

Akutsu-Shigeno, Y. et al. "Cloning and Sequencing of a Poly($_{DL}$-Lactic Acid) Depolymerase Gene from *Paenibacillus amylolyticus* Strain TB-13 and Its Functional Expression in *Escherichia coli*" *Applied and Environmental Microbiology*, May 2003, pp. 2498-2504, vol. 69, No. 5.

Petrov, K. et al. "$_L$(+)-Lactic acid production from starch by a novel amylolytic *Lactococcus lactis* subsp. *lactis* 884" *Food Microbiology*, Jun. 2008, pp. 550-557, vol. 25.

Currently pending claims of U.S. Appl. No. 14/443,524, 2016, pp. 1-4.

Bernard, N. et al. "Cloning of the D-lactate dehydrogenase gene from *Lactobacillus delbrueckii* subsp. *bulgaricus* by complementation in *Escherichia coli*" *FEBS*, Sep. 1991, pp. 61-64, No. 1.

Wieczorek, A. et al. "Engineering the cell surface display of cohesins for assembly of cellulosome-inspired enzyme complexes on *Lactococcus lactis*" *Microbial Cell Factories*, Sep. 2010, pp. 1-13, Vo. 9, No. 69.

Wieczorek, A. et al. "Effects of synthetic cohesin-containing scaffold protein architecture on binding dockerin-enzyme fusions on the surface of *Lactococcus lactis*" *Microbial Cell Factories*, 2012, pp. 1-13, vol. 160, No. 11.

Koukiekolo, R. et al. "Degradation of Corn Fiber by *Clostridium cellulovorans* Cellulases and Hemicellulases and Contribution of Scaffolding Protein CbpA" Applied and Environmental Microbiology, Jul. 1, 2005, pp. 3504-3511, vol. 71, No. 7.

Cha, J. et al. "Effect of Multiple Copies of Cohesins on Cellulase and Hemicellulase Activities of *Clostridium cellulovorans* Minicellulosomes" *Journal of Microbiology and Biotechnology*, 2007, pp. 1782-1788, vol. 17, No. 11.

Kataeva, I. et al. "Interaction between *Clostridium thermocellum* endoglucanase CelD and polypeptides derived from the cellulosome-integrating protein CipA: stoichiometry and cellulolytic activity of the complexes" *Biochemical Journal*, 1997. pp. 617-624, vol. 326, No. 2.

Wen, F. et al. "Yeast Surface Display of Trifunctional Minicellulosomes for Simultaneous Saccharification and Fermentation of Cellulose to Ethanol" Applied and Environmental Microbiology, Feb. 1, 2010, pp. 1251-1260, vol. 76, No. 4.

Hyeon, J. E. et al. "Production of minicellulosomes for the enhanced hydrolysis of cellulosic substrates by recombinant *Corynebacterium glutamicum*" *Enzyme and Microbial Technology*, 2011, pp. 371-377, vol. 48.

Sun, J. et al. "Direct Conversion of Xylan to Ethanol by Recombinant *Saccharomyces cerevisiae* Strains Displaying an Engineered Minihemicellulosome" Applied and Environmental Microbiology, Jun. 2012, pp. 3837-3845, vol. 78, No. 11.

Database EMBL [Online] Accession No. HC441374, "Sequence 9 from Patent WO2010012805" Feb. 20, 2010, pp. 1-3, XP-002697306.

Database Geneseq [Online] Accession No. AZM34659, "*Clostridium* sp. Cellulose-binding protein-A (CbpA) DNA SEQ: 6" Oct. 13, 2011, p. 1, XP-002697307.

Written Opinion in International Application No. PCT/EP2013/061413, Aug. 5, 2013, pp. 1-7.

Devos, D. et al. "Practical Limits of Function Prediction" *Proteins: Structure, Function and Genetics*, 2000, pp. 98-107, vol. 41.

(56) References Cited

OTHER PUBLICATIONS

Whisstock, J. C. et al. "Prediction of protein function from protein sequence and structure" *Quarterly Reviews of Biophysics*, 2003, pp. 307-340, vol. 36, No. 3.
Witkowski, A. et al. "Conversion of a β-Ketoacyl Synthase to a Malonyl Decarboxylase by Replacement of the Active-Site Cysteine with Glutamine" *Biochemistry*, 1999, pp. 11643-11650, vol. 38.
Kisselev, L. "Polypeptide Release Factors in Prokaryotes and Eukaryotes: Same Function, Different Structure" *Structure*, Jan. 2002, pp. 8-9, vol. 10.
Database WPI, Accession No. 2005-262580, Mar. 24, 2005, pp. 1-3, XP-002690554.
Database WPI, Accession No. 2004-751104, Oct. 21, 2004, pp. 1-2, XP-002690555.
Currently pending claims of U.S. Appl. No. 14/387,285, 2014, pp. 1-3.
Yoshida, S. et al. "A bacterium that degrades and assimilates poly(ethylene terephthalate)" *Science*, Mar. 11, 2016, pp. 1196-1199, vol. 351.
Demirel, B. et al. "Crystallization Behavior of PET Materials" *BAU Fen Bil. Enst. Dergisi Cilt*, 2011, pp. 26-35, vol. 13, No. 1.
Kyrikou, I. et al. "Biodegradation of Agricultural Plastic Films: A Critical review" *J Polym Environ*, 2007, pp. 125-150, vol. 15.
Chen, S. et al. "Identification and Characterization of Bacterial Cutinase" *The Journal of Biological Chemistry*, Sep. 19, 2008, pp. 25854-25862, vol. 238, No. 38.
Ronkvist, A. M. et al. "Cutinase-Catalyzed Hydrolysis of Poly(ethylene terephthalate)" *Macromolecules*, 2009, pp. 5128-5138, vol. 42.
Nabil, H. et al. "Recycled Polyethylene Terephthalate Filled Natural Rubber Compounds: Effects of Filler Loading and Types of Matrix" *Journal of Elastomers and Plastics*, 2011, pp. 1-21, vol. 00-2011.
Bartolome, L. et al. "Recent Developments in the Chemical Recycling of PET" Material Recycling—Trends and Perspectives, Mar. 16, 2012, pp. 1-21.
Arutchelvi, J. et al. "Biodegradation of polyethylene and polypropylene" *Indian Journal of Biotechnology*, Jan. 2008, pp. 9-22, vol. 7.
Iwamoto, A. et al. "Enzymatic degradation of plastics containing polycaprolactone" *Polymer Degradation and Stability*, Jan. 1, 1994, pp. 205-213, vol. 45.
Mueller, R.-J. "Biological degradation of synthetic polyesters—Enzymes as potential catalysts for polyester recycling" *Process Biochemistry*, 2006, pp. 2124-2128, vol. 41, No. 10.
Written Opinion in International Application No. PCT/EP2014/073742, Aug. 8, 2015, pp. 1-5.
Gouda, M. K. et al. "Production of a Polyester Degrading Extracellular Hydrolase from *Thermomonospora fusca*" *Biotechnology Progress*, Sep. 2002, pp. 927-934, vol. 18, No. 5.
Oda, Y. et al. "Degradation of Polylactide by Commercial Proteases" *Journal of Polymers and the Environment*, Jan. 2000, pp. 29-32, vol. 8, No. 1.
Written Opinion in International Application No. PCT/EP2016/055348, Jun. 2, 2016, pp. 1-6.
Database UniProt [Online] Accession No. I0LED3, Jun. 13, 2012, pp. 1-2, XP-002743807.
Database Geneseq [Online] Accession No. BAJ28992, Jan. 31, 2013, pp. 1-10, XP-002743803.
Database Geneseq [Online] Accession No. BAJ28991, Jan. 31, 2013, pp. 1-2, XP-002743804.
Database UniProt [Online] Accession No. F4F956, Jun. 28, 2011, pp. 1-2, XP-002743805.
Database UniProt [Online] Accession No. A8LWF7, Dec. 4, 2007, p. 1-2, XP-002743806.
Albertsson, A-C. et al. "Chemistry and biochemistry of polymer biodegradation" *Chemistry and Technology of Biodegradable Polymers*, Jan. 1, 1994, pp. 7-17, Section 2.
Database WPI [Online] Accession No. 2012-Q50933, Sep. 9, 2012, p. 1, XP-002740253.
Database WPI [Online] Accession No. 2004-046313, May 8, 2003, pp. 1-2, XP-002740254.
Written Opinion in International Application No. PCT/EP2015/080557, Feb. 3, 2016, pp. 1-6.
Written Opinion in International Application No. PCT/EP2016/063369, Aug. 1, 2016, pp. 1-6.
Written Opinion in International Application No. PCT/EP2016/063373, Aug. 8, 2017, pp. 1-7.
Okino, S. et al. "Production of $_D$-lactic acid by *Corynebacterium glutamicum* under oxygen deprivation" *Applied Microbiology and Biotechnology*, Jan. 10, 2008, pp. 449-454, vol. 78, No. 3.
Database WPI [Online] Accession No. 2012-K88398, Jan. 27, 2011, pp. 1-2, XP-002759107.
Written Opinion in International Application No. PCT/EP2016/081205, Jun. 1, 2017, pp. 1-19.
Written Opinion in International Application No. PCT/EP2017/062028, Jun. 30, 2017, pp. 1-5.
Herrero Acero, E. et al. "Enzymatic Surface Hydrolysis of PET: Effect of Structural Diversity on Kinetic Properties of Cutinases from *Thermobifida*" *Macromolecules*, 2011, pp. 4632-4640, vol. 44, No. 12.
Herrero Acero, E. et al. "Surface Engineering of a Cutinase From *Thermobifida Cellulosilytica* for Improved Polyester Hydrolysis" *Biotechnology & Bioengineering*, Oct. 2013, pp. 2581-2590, vol. 110, No. 10.
Shah, A. A. et al. "Degradation of aliphatic and aliphatic-aromatic co-polyesters by depolymerases from *Roseateles depolymerans* strain TB-87 and analysis of degradation products by LC-MS" *Polymer Degradation and Stability*, Oct. 16, 2013, pp. 2722-2729, vol. 98, No. 12.
Written Opinion in International Application No. PCT/EP2015/060521, Jul. 20, 2015, pp. 1-6.
Wikipedia, https://web.archive.org/web/20130424032652/https://en.wikipedia.org/wiki/Polyethylene_terephthalate, archived Apr. 24, 2013, accessed Aug. 13, 2018, pp. 1-13.
Currently pending claims of U.S. Appl. No. 16/302,107, filed 2018, pp. 1-4.
Currently pending claims of U.S. Appl. No. 16/064,494, filed 2018, pp. 1-3.

\* cited by examiner

SEQUENCE LISTING

```
<160> NUMBER OF SEQ ID NOS: 5

<210> SEQ ID NO 1
<211> LENGTH: 276
<212> TYPE: PRT
<213> ORGANISM: artificial sequence
<220> FEATURE:
<223> OTHER INFORMATION: PAM Polypeptide

<400> SEQUENCE: 1

Ala Thr Gln Asn Asn Pro Pro Ser Trp Gly Leu Asp Arg Ile Asp Gln
1               5                   10                  15

Thr Asn Leu Pro Leu Ser Arg Ser Tyr Thr Tyr Asn Ser Thr Gly Ala
            20                  25                  30

Gly Val Asn Ala Tyr Ile Ile Asp Thr Gly Ile Tyr Thr Ala His Ser
        35                  40                  45

Asp Phe Gly Gly Arg Ala Thr Asn Val Tyr Asp Ala Leu Gly Gly Asn
    50                  55                  60

Gly Gln Asp Cys Asn Gly His Gly Thr His Val Ala Gly Thr Val Gly
65                  70                  75                  80

Gly Ala Ala Tyr Gly Val Ala Lys Ala Val Asn Leu Arg Gly Val Arg
                85                  90                  95

Val Leu Asn Cys Ser Gly Ser Gly Thr Thr Ser Gly Val Ile Ala Gly
            100                 105                 110

Met Asn Trp Val Ala Ser Asn His Val Lys Pro Ala Val Ala Asn Met
        115                 120                 125
```

```
Ser Leu Gly Gly Gly Tyr Ser Ser Leu Asn Thr Ala Ala Asn Asn
    130                 135                 140

Leu Ala Ser Ser Gly Val Phe Leu Ala Val Ala Ala Gly Asn Glu Thr
145                 150                 155                 160

Thr Asn Ala Cys Asn Arg Ser Pro Ala Ser Ala Asn Ala Thr Thr
            165                 170                 175

Val Ala Ala Ser Thr Ser Thr Asp Ala Arg Ala Ser Tyr Ser Asn Tyr
            180                 185                 190

Gly Ser Cys Val His Leu Tyr Ala Pro Gly Ser Ser Ile Thr Ser Ala
            195                 200                 205

Trp Leu Asn Gly Gly Thr Asn Thr Ile Ser Gly Thr Ser Met Ala Thr
    210                 215                 220

Pro His Val Ala Gly Thr Ala Ala Leu Tyr Lys Ala Thr Tyr Gly Asp
225                 230                 235                 240

Ala Ser Phe Ser Thr Ile Arg Ser Trp Leu Val Ser Asn Ala Thr Ser
                245                 250                 255

Gly Val Ile Thr Gly Asn Val Ser Gly Thr Pro Asn Leu Leu Leu Asn
            260                 265                 270

Lys Arg Ser Leu
        275

<210> SEQ ID NO 2
<211> LENGTH: 828
<212> TYPE: DNA
<213> ORGANISM: artificial sequence
<220> FEATURE:
<223> OTHER INFORMATION: PAM nucleic acid sequence

<400> SEQUENCE: 2
gccacgcaga acaacccgcc gtcgtggggc ctggaccgca tcgaccagac gaacctgccg      60
ctgtcgcgca gctacaccta caattccacc ggcgcgggcg tgaacgccta catcatcgac     120
accggcatct acaccgcgca ctccgacttc ggcggccgcg ccaccaacgt ctacgacgcc     180
ctcggcggca acggccagga ctgcaacggc acggcaccc acgtcgcggg caccgtcggc     240
ggcgccgcct acggcgtggc caaggcggtc aacctgcgcg cgtgcgcgt gctcaactgc     300 agcggcagcg gcaccaccct cggtgtcatc gccggcatga actgggtggc cagcaaccac     360
gtcaagcccg ccgtggcgaa catgtcgctg gcggcggct actcctcctc cctgaacacg     420
gccgccaaca acctggccag ctccggcgtg ttcctggccg tcgccgcggg caacgagacc     480
accaacgcct gcaaccgctc gccggccagc gccgccaacg ccaccaccgt cgccgcgagc     540
accagcaccg acgcccgggc ctcctacagc aactacggct cgtgcgtcca cctgtacgcg     600
cccggctcgt ccatcacctc cgcctggctg aacggcggca ccaacaccat cagcggcacg     660
tcgatggcca cgccgcacgt ggccgggacc gccgccctct acaaggcgac ctacggcgac     720
gcctcgttca gcaccatccg cagctggctg gtcagcaacg ccacctccgg cgtcatcacc     780
ggcaacgtgt cgggcacccc gaacctgctg ctgaacaagc gctccctg                 828

<210> SEQ ID NO 3
<211> LENGTH: 28
<212> TYPE: PRT
<213> ORGANISM: artificial sequence
<220> FEATURE:
<223> OTHER INFORMATION: N-terminal polypeptide sequence

<400> SEQUENCE: 3

Ala Thr Gln Asn Asn Pro Pro Ser Trp Gly Leu Asp Arg Ile Asp Gln
```

Thr Asn Leu Pro Leu Ser Arg Ser Tyr Thr Tyr Asn
            20                  25

<210> SEQ ID NO 4
<211> LENGTH: 1161
<212> TYPE: DNA
<213> ORGANISM: artificial sequence
<220> FEATURE:
<223> OTHER INFORMATION: DNA sequence

<400> SEQUENCE: 4

```
atgagacgac gtaccctgcc catcgccgtc ctcgccgccg ttcccctggc cgtggcgggc      60
gccctgcccg ccggagccgc cccgccgcc cccgccgtcc cggtcgccat ggcggccgcc     120
ggacagggcg tcgccggaca gtacatcgtg acgctgaaga agggcgtctc ggtcgactcg     180
accgtcgcca agcgcggaat ccgcacccag caccgtttcg gcaaggtgct gaacggcttc     240
tccgccaagc tcaccgatga ccaactgtcc aagctgcgca ccgcccgg tgtcgcgtcc      300
atcgagcagg acgccgtcat cacggtggac gccacgcaga caacccgcc gtcgtgggc      360
ctggaccgca tcgaccagac gaacctgccg ctgtcgcgca gctacaccta caattccacc     420
ggcgcgggcg tgaacgccta catcatcgac accggcatct acaccgcgca ctccgacttc     480
ggcgccgcg ccaccaacgt ctacgacgcc ctcggcggca acggccagga ctgcaacggc      540
cacggcaccc acgtcgcggg caccgtcggc ggcgccgcct acggcgtggc caaggcggtc     600
aacctgcgcg gcgtgcgcgt gctcaactgc agcggcagcg gcaccacctc cggtgtcatc     660
gccggcatga actgggtggc cagcaaccac gtcaagcccg ccgtggcgaa catgtcgctg     720
ggcggcggct actcctcctc cctgaacacg gccgccaaca acctggccag ctccggcgtg     780
ttcctggccg tcgccgcggg caacgagacc accaacgcct gcaaccgctc gccggccagc     840
gccgccaacg ccaccacggt cgccgcgagc accagcaccg acgcccgggc ctcctacagc     900
aactacggct cgtgcgtcca cctgtacgcg cccggctcgt ccatcacctc cgcctggctg     960
aacgcggca ccaacaccat cagcggcacg tcgatggcca cgccgcacgt ggccgggacc     1020
gccgccctct acaaggcgac ctacggcgac gcctcgttca gcaccatccg cagctggctg     1080
gtcagcaacg ccacctccgg cgtcatcacc ggcaacgtgt cgggcacccc gaacctgctg     1140
ctgaacaagc gctccctgta a                                                1161
```

<210> SEQ ID NO 5
<211> LENGTH: 386
<212> TYPE: PRT
<213> ORGANISM: artificial sequence
<220> FEATURE:
<223> OTHER INFORMATION: Polypeptide sequence

<400> SEQUENCE: 5

Met Arg Arg Arg Thr Leu Pro Ile Ala Val Leu Ala Ala Val Pro Leu
1               5                   10                  15

Ala Val Ala Gly Ala Leu Pro Ala Gly Ala Ala Pro Ala Ala Pro Ala
            20                  25                  30

Val Pro Val Ala Met Ala Ala Ala Gly Gln Gly Val Ala Gly Gln Tyr
        35                  40                  45

Ile Val Thr Leu Lys Lys Gly Val Ser Val Asp Ser Thr Val Ala Lys
    50                  55                  60

Arg Gly Ile Arg Thr Gln His Arg Phe Gly Lys Val Leu Asn Gly Phe
65                  70                  75                  80

-continued

```
Ser Ala Lys Leu Thr Asp Asp Gln Leu Ser Lys Leu Arg Thr Thr Pro
                85                      90                  95
Gly Val Ala Ser Ile Glu Gln Asp Ala Val Ile Thr Val Asp Ala Thr
                100                     105                 110
Gln Asn Asn Pro Pro Ser Trp Gly Leu Asp Arg Ile Asp Gln Thr Asn
                115                     120                 125
Leu Pro Leu Ser Arg Ser Tyr Thr Tyr Asn Ser Thr Gly Ala Gly Val
    130                     135                 140
Asn Ala Tyr Ile Ile Asp Thr Gly Ile Tyr Thr Ala His Ser Asp Phe
145                     150                 155                 160
Gly Gly Arg Ala Thr Asn Val Tyr Asp Ala Leu Gly Gly Asn Gly Gln
                165                     170                 175
Asp Cys Asn Gly His Gly Thr His Val Ala Gly Thr Val Gly Gly Ala
                180                     185                 190
Ala Tyr Gly Val Ala Lys Ala Val Asn Leu Arg Gly Val Arg Val Leu
            195                     200                 205
Asn Cys Ser Gly Ser Gly Thr Thr Ser Gly Val Ile Ala Gly Met Asn
    210                     215                 220
Trp Val Ala Ser Asn His Val Lys Pro Ala Val Ala Asn Met Ser Leu
225                     230                     235                 240
Gly Gly Gly Tyr Ser Ser Ser Leu Asn Thr Ala Ala Asn Asn Leu Ala
                245                     250                 255
Ser Ser Gly Val Phe Leu Ala Val Ala Ala Gly Asn Glu Thr Thr Asn
            260                     265                 270
Ala Cys Asn Arg Ser Pro Ala Ser Ala Ala Asn Ala Thr Thr Val Ala
        275                     280                 285
Ala Ser Thr Ser Thr Asp Ala Arg Ala Ser Tyr Ser Asn Tyr Gly Ser
    290                     295                 300
Cys Val His Leu Tyr Ala Pro Gly Ser Ser Ile Thr Ser Ala Trp Leu
305                 310                     315                 320
Asn Gly Gly Thr Asn Thr Ile Ser Gly Thr Ser Met Ala Thr Pro His
                325                     330                 335
Val Ala Gly Thr Ala Ala Leu Tyr Lys Ala Thr Tyr Gly Asp Ala Ser
                340                     345                 350
Phe Ser Thr Ile Arg Ser Trp Leu Val Ser Asn Ala Thr Ser Gly Val
                355                     360                 365
Ile Thr Gly Asn Val Ser Gly Thr Pro Asn Leu Leu Leu Asn Lys Arg
    370                     375                 380
Ser Leu
385
```

US 10,287,561 B2

POLYPEPTIDE HAVING A POLYESTER DEGRADING ACTIVITY AND USES THEREOF

CROSS-REFERENCE TO RELATED APPLICATION

This application is the U.S. national stage application of International Patent Application No. PCT/EP2015/074222, filed Oct. 20, 2015.

The Sequence Listing for this application is labeled "Seq-List.txt" which was created on Apr. 6, 2017 and is 10 KB. The entire content of the sequence listing is incorporated herein by reference in its entirety.

FIELD OF THE INVENTION

The present invention relates to a novel polypeptide having an enzymatic activity and the uses thereof. The invention also relates to methods of producing such polypeptide, coding nucleic acid molecule, recombinant cells and methods of degrading polyester-containing material with use of such polypeptide. The polypeptide of the invention is particularly suited to degrade polylactic acid, and material containing polylactic acid, as plastic material.

BACKGROUND OF THE INVENTION

Polyesters are used in a large number of technical fields, in particular in the form of plastic material, from food packaging to the medical field, via clothing, the automobile industry, etc. As an example, certain polyesters (for example polyethylene terephthalate—PET, polylactic acid—PLA, etc.) are used in the manufacture of clothes and packaging, but also in the form of a thermoset resin for the manufacture of automobile or other parts.

As a consequence, the production of polyester containing plastics has increased dramatically over the last decades. More than 50% of these plastics are used for single-use disposable applications, such as packaging, agricultural films, disposable consumer items or for short-lived products that are discarded within a year of manufacture. Regrettably, plastics may persist for decades depending on local environmental factors, like levels of ultraviolet light exposure, temperature, presence of suitable microorganisms, etc. As a consequence, substantial quantities of plastics are piling up in landfill sites and in natural habitats worldwide, generating increasing environmental problems.

One solution to reduce environmental and economic impacts correlated to the accumulation of plastic is recycling wherein plastic material is mechanically reprocessed to manufacture new products. However, the actual recycling processes use huge amounts of electricity, particularly during the extruding step, and the equipment used is also expensive, leading to high prices which may be non-competitive compared to virgin plastic.

Another potential process for recycling plastic consists of chemical recycling allowing recovering the chemical constituents of the polymer. The resulting monomers may then be used to re-manufacture plastic or to make other synthetic chemicals. However, up to now, such recycling process has only been performed on purified polymers and is not efficient on raw plastic products constituted of a mix of crystallized and amorphous polymers and additives. Moreover, such recycling process is expensive leading to non-competitive monomers compared to virgin monomers.

On the other hand, enzymatic degradation is looked as an ideal waste treatment method because enzymes can accelerate hydrolysis of plastics and can be incorporated into a natural cycle of organic materials. Furthermore, the hydrolysate (i.e., monomers and oligomers) can be recycled as material for polymers. Thus, the depolymerization of polymers contained in a plastic product by enzymes is of great interest, as an alternative to the existing and unsatisfactory processes.

However, this approach did not lead so far to the implementation of an effective and industrial enzymatic method of degrading polyester containing material.

Indeed, many bacteria are known to have the ability to degrade polyesters. For instance, regarding polylactic acid, there is a report of degrading enzymes derived from *Actinomycetes* such as *Amycolatopsis* sp. (strain K104-1) and from *Paenibacillus amylolyticus* (strain TB-13). However, up to now, the identified polypeptides have poor degrading ability and allow only degradation of the polymer in emulsion form. There is a limited number of reports on microorganisms capable of degrading polyester-containing material in film or pellet form, and further their enzymes are poorly known.

In view of the foregoing, there is a need for novel enzymes active in the degradation of polyester and more particularly in the degradation of polyesters contained in plastic products.

SUMMARY OF THE INVENTION

Work conducted by the applicant has led to the identification of a novel polypeptide derived from *Actinomadura* sp. and having a polyester degrading activity. This polypeptide had never been reported or isolated in the art and brings substantial improvements to the development of industrial processes of degrading polyester containing material.

The invention stems inter alia from the identification of this new polypeptide, having the remarkable property of degrading polyester. The invention relates to a solution to obtaining on an industrial scale the degradation of polyesters contained in a plastic product, whom degradation products (monomers and oligomers) can be reused to produce new polyesters both economically and reliably.

Thus, the present invention relates to novel polypeptides having an enzymatic activity, their manufacture and uses. The invention also relates to nucleic acids encoding these polypeptides, vectors, recombinant cells expressing these polypeptides and their uses. The invention further relates to compositions comprising at least one polypeptide of the invention and to methods for producing oligomers and/or monomers of interest from a polyester containing material such as a plastic product made of polyester. The invention also relates to biodegradable plastic compounds or plastic articles containing at least one of these polypeptides and/or recombinant cells expressing these polypeptides.

An object of this invention thus relates to an isolated polypeptide comprising an amino acid sequence having at least 94%, 95%, 99% or 100%, preferably at least 95%, 96%, 97%, 98%, 99% or 100% identity to the full length amino acid sequence set forth in SEQ ID NO: 1, and having a polyester degrading activity.

In a particular embodiment, the amino acid residue sequence of the polypeptide differs from SEQ ID NO: 1 by an amino acid residue substitution of an amino acid residue at one or more positions. In a preferred embodiment, the amino acid residue substitution introduces cysteine(s) or extra-salt bridges in the amino acid residue sequence and thereby increases the thermostability of the polypeptide compared to the thermostability of the native polypeptide (i.e., polypeptide having the amino acid residue sequence set forth in SEQ ID NO: 1).

It is a further object of the invention to provide a polypeptide comprising the amino acid sequence set forth in SEQ ID NO: 1 or SEQ ID NO: 5.

In a particular embodiment, the polypeptide comprises one or several glycosylated amino acid residues.

A further object of this invention is a nucleic acid coding a polypeptide as defined above. The invention also relates to an expression cassette comprising a nucleic acid as defined above and to a vector comprising a nucleic acid or expression cassette as defined above.

The invention also relates to a recombinant cell, or host cell, preferably a recombinant microorganism, containing at least one nucleic acid or expression cassette or vector as defined above, and to extracts thereof that preferably exhibit the enzymatic activity.

It is another object of the invention to provide a method of producing the polypeptide of the invention, comprising (i) culturing a recombinant cell as defined above, (ii) recovering the culture supernatant, and optionally (iii) isolating or purifying the polypeptide.

The invention also discloses a composition comprising a polypeptide or a recombinant cell expressing the polypeptide or an extract thereof, as defined above.

The invention further relates to the use of a polypeptide, corresponding nucleic acid, expression cassette, vector, recombinant cell, recombinant cell extract, or composition as defined above for the enzymatic degradation of a polyester containing material, preferably a PLA containing material, even more preferably a PLLA containing material.

It is a further object of the invention to provide a method for degrading a polyester containing material, wherein a polyester containing material is contacted with a polypeptide, corresponding nucleic acid, expression cassette, vector, recombinant cell or recombinant cell extract, or composition as defined above. The method advantageously further comprises a step of collecting the resulting monomers and/or oligomers.

The invention also relates to a method for producing monomers and/or oligomers from a polyester containing material, comprising exposing a polyester containing material to a polypeptide, corresponding nucleic acid, expression cassette, vector, recombinant cell or recombinant cell extract, or composition as defined above, and optionally recovering monomers and/or oligomers.

It is another object of the invention to provide a polyester containing material comprising a polypeptide and/or a recombinant cell expressing the polypeptide as defined above.

The invention also provides a process for producing such polyester containing material comprising a step of mixing a polyester and a polypeptide and/or a recombinant cell expressing the polypeptide as defined above, wherein the mixing step is performed at a temperature at which the polyester is in a partially or totally molten state, preferably during an extrusion process.

The invention further relates to the use of a polypeptide comprising an amino acid sequence having at least 75%, 80%, 85%, 90%, 92%, 95%, 99% or 100% identity to the full length amino acid sequence set forth in SEQ ID NO: 1, and having a polyester degrading activity for degrading a polyester containing material.

LEGEND TO THE FIGURES

FIG. 1. A picture of a SDS-Page gel of a pH 10 flow-through from anionic purification, showing that the molecular weight of the polypeptide of the invention is 27 kDa.

Figure 2:
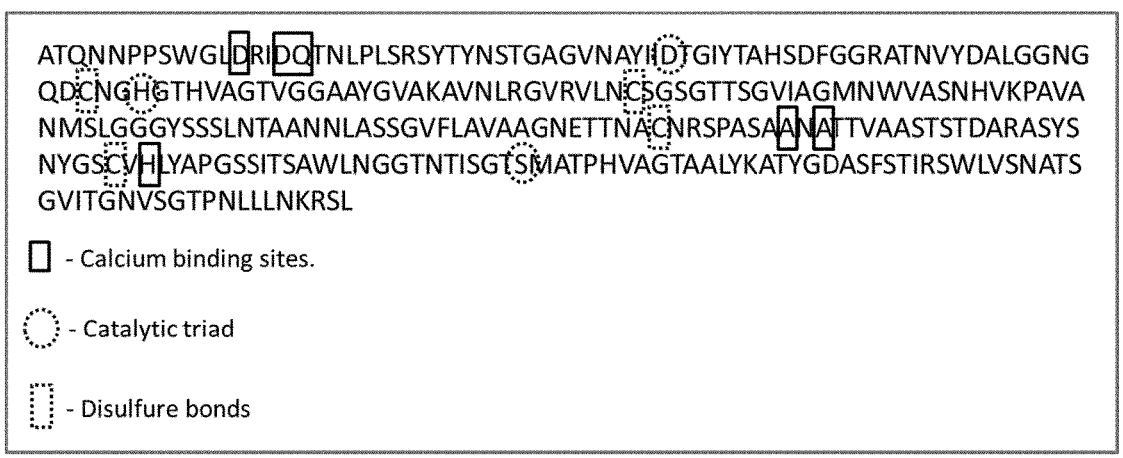

FIG. 2. The amino acid sequence of a polypeptide of the invention (SEQ ID NO: 1), with the most significant residues highlighted.

Figure 3:
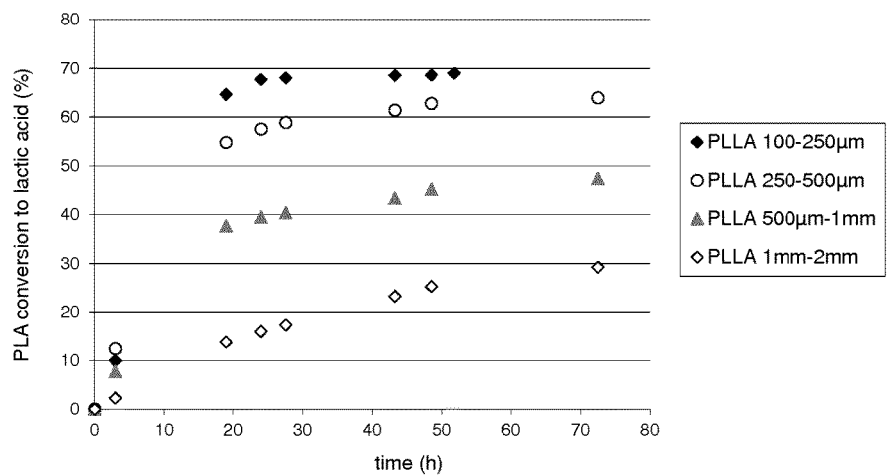

FIG. 3: A graph showing the polyesterase-catalyzed hydrolysis of NaturePlast PLLA powder (33 g/L) and the production of lactic acid, in function of PLLA particle size.

Figure 4:
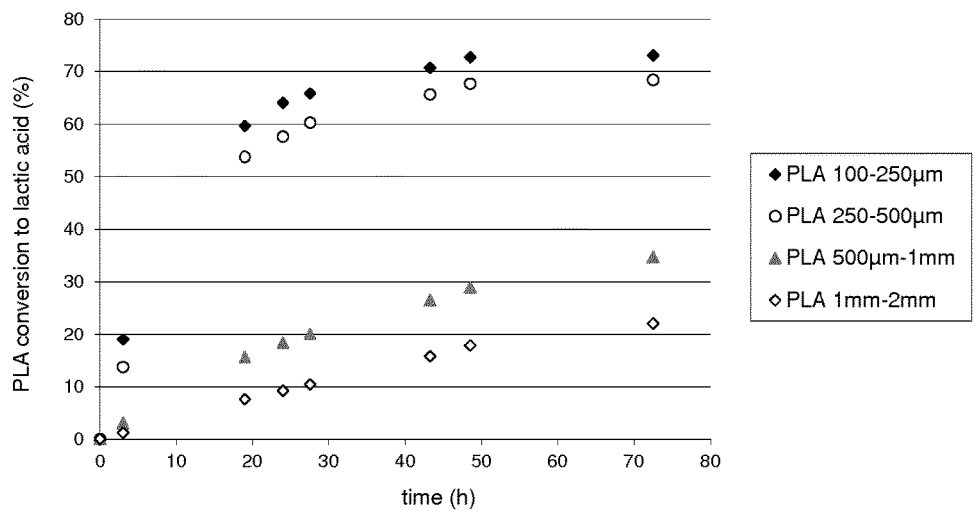

FIG. 4: A graph showing the polyesterase-catalyzed hydrolysis of an INGEO 7001D PLA powder (33 g/L) and the production of lactic acid, in function of PLA particle size.

Figure 5:
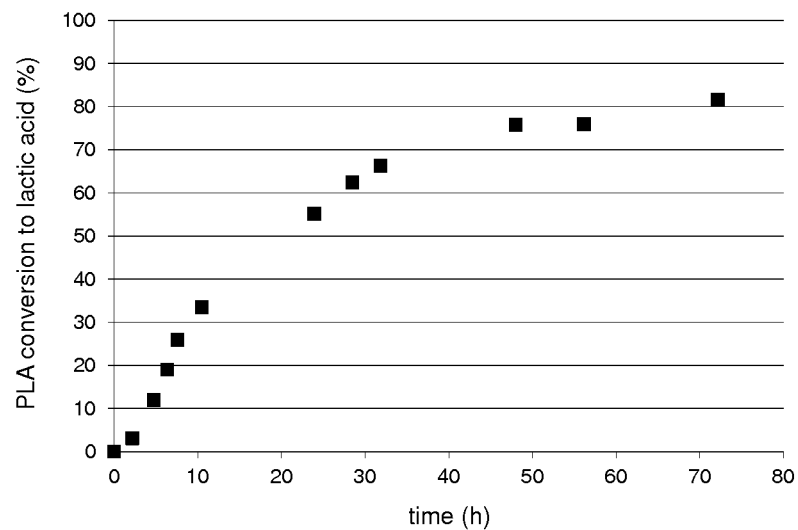

FIG. 5: A graph showing the polyesterase-catalyzed hydrolysis of PLA film (17 g/L) and the production of lactic acid.

Figure 6:
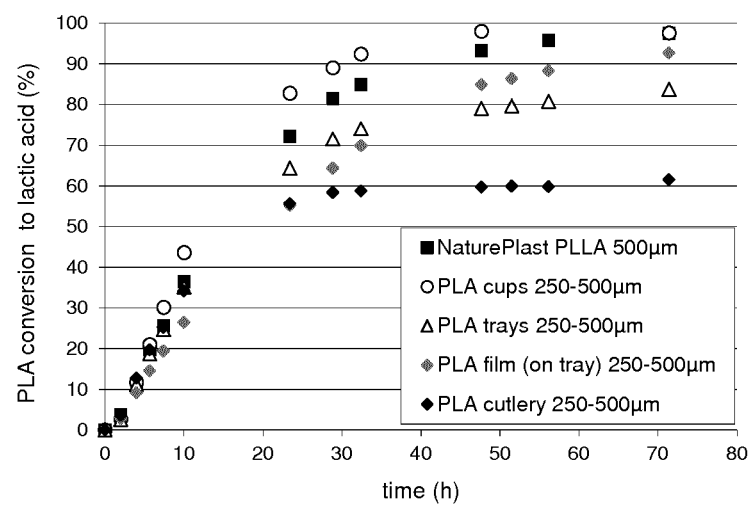

FIG. 6: A graph showing the polyesterase-catalyzed hydrolysis of PLA commercial objects (PLA cups, trays, film and cutlery) (33 g/L)) and the production of lactic acid.

Figure 7:
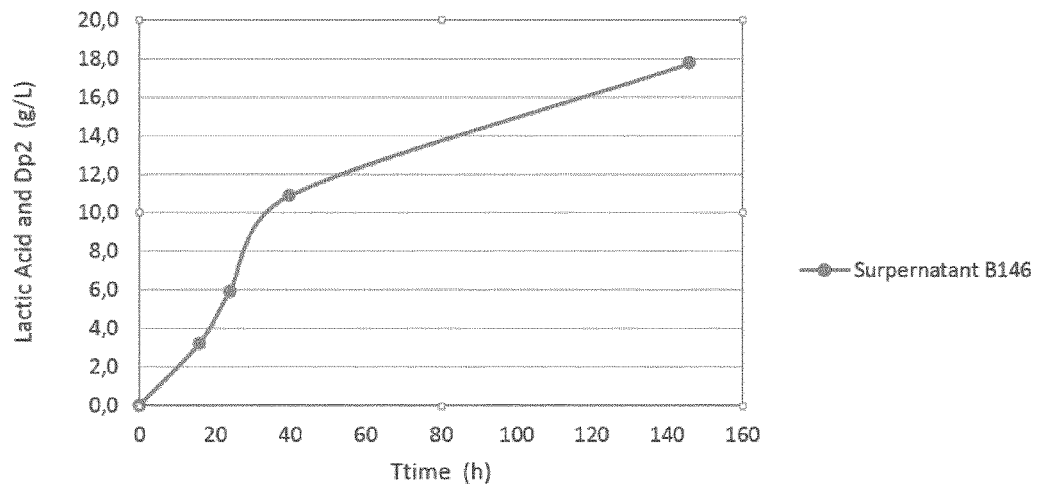

FIG. 7: A graph showing the hydrolysis of PLA in a medium comprising $CaCO_3$ and $Ca(OH)_2$.

Figure 8:
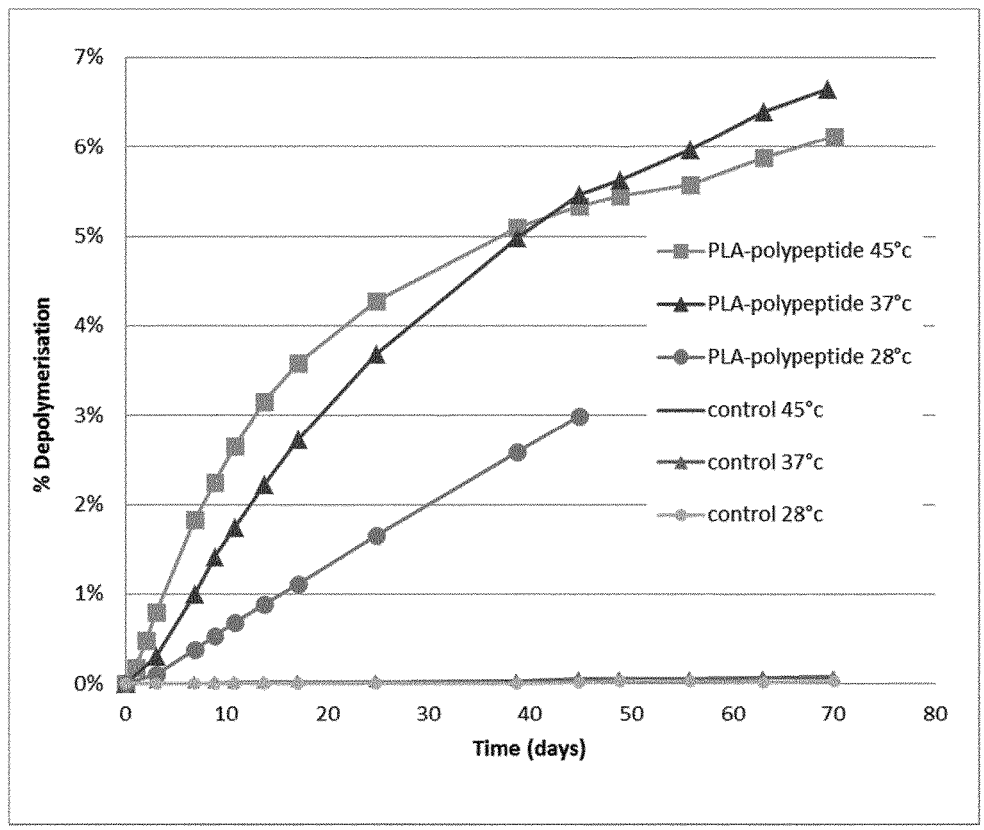

FIG. 8: A graph showing the hydrolysis of PLA containing materials containing 96% PLA and 4% of the polypeptide of the invention and the hydrolysis of Controls containing 100% PLA, at 28° C., 37° C. and 45° C. in Tris buffer at pH 9.5.

DETAILED DESCRIPTION OF THE INVENTION

The invention relates, generally, to an isolated polypeptide comprising at least a biologically active part of the amino acid sequence set forth in SEQ ID NO: 1, which is able to depolymerize polyesters, more preferably polylactic acid. This polypeptide, which is preferably active at a temperature range from 20° C. to 90° C., and at least from 20° C. to 60° C., can be used to degrade a polyester plastic material. This polypeptide, or its coding nucleic acid sequence, may also be used to create a recombinant microorganism, which may serve to cause degradation of polyester containing material. Such recombinant microorganism may further exhibit a natural or recombinant polymer synthesis activity, so that said microorganism is able to reuse the monomers and/or oligomers resulting from the polyester degradation.

The following is a description of the present invention, including preferred embodiments thereof given in general terms. The present invention is further exemplified in the disclosure given under the heading "Examples" herein below, which provides experimental data supporting the invention and means of performing the invention.

Definitions

The present disclosure will be best understood by reference to the following definitions.

The term "isolated" or "isolation" means that the material is removed from its original environment (e.g., the natural environment). For instance, an isolated polypeptide is typically devoid of at least some polypeptides or other constituents of the cells to which it is normally associated or with which it is normally admixed or in solution. An isolated polypeptide includes said naturally-produced polypeptide in a purified or partially purified form, the recombinant polypeptide, the polypeptide which is expressed or secreted by a host cell, as well as the polypeptide in a host cell or culture or extract thereof. In a preferred aspect, the polypeptide is at least 10% pure, preferably at least 50% pure, more preferably at least 60%, 70%, 80%, 90% pure, as determined by SDS-PAGE. A purity less than 100% denotes herein a polypeptide preparation that contains other polypeptide material which it is natively or recombinantly associated. In relation to a nucleic acid, the term isolated or purified indicates e.g., that the nucleic acid is not in its natural genomic context (e.g., in a vector, an expression cassette, linked to a promoter, or artificially introduced in a heterologous host cell).

The term "modification" means herein any chemical modification of the polypeptide consisting of SEQ ID NO: 1 or a homologous sequence thereof, as well as genetic manipulation of the DNA encoding such a polypeptide. The modification can be a substitution, a deletion and/or an insertion of one or several amino acids. Accordingly, the terms "mutant" and "variant" may be used interchangeably to refer to polypeptides consisting of SEQ ID NO: 1 with identified amino acid substitution(s), deletion(s) and/or insertion(s) at determined residue(s).

A term "glycosylated" means that the material comprises one or several glycans attached to amino acid residue(s) of the polypeptide. In the context of the invention, the glycosylation encompasses N-linked glycans, attached to the amide nitrogen of asparagine residue, O-linked glycans attached to the hydroxyl oxygen of serine or tyrosine residues, C-linked glycans attach to a carbon of a tryptophan residue.

The term "recombinant" refers to a nucleic acid construct, a vector, a polypeptide or a cell produced by genetic engineering.

As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as blast.ncbi.nlm.nih.gov/or Worldwide Website: ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

The term "expression", as used herein, refers to any step involved in the production of a polypeptide including, but being not limited to, transcription, post-transcriptional modification, translation, post-translational modification, and secretion.

Herein, the terms "peptide", "polypeptide", "protein" and "enzyme" are employed interchangeably and refer to a chain of amino acids linked by peptide bonds, regardless of the number of amino acids forming said chain. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

In the context of the invention, a "polyester containing material" refers to a product, such as plastic product, comprising at least one polyester in crystalline, semi-crystalline or totally amorphous forms. In a particular embodiment, the polyester containing material refers to any item made from at least one plastic material, such as plastic sheet, tube, rod, profile, shape, film, massive block etc., which contains at least one polyester, and possibly other substances or additives, such as plasticizers, mineral or organic fillers. In a particular embodiment, the polyester containing material contains polyester and at least one additional polymer, such as a polyolefin, arranged relative to each other in such a way that they cannot be easily separated. Preferably the polyester containing material is constituted of a mix of crystallized and amorphous polyesters, and/or semi-crystallized polyesters, and additives. More preferably, the polyester containing material is a manufactured plastic product like packaging, agricultural films, disposable items or the like. In another particular embodiment, the polyester containing material refers to a plastic compound, or plastic formulation, in a molten or solid state, suitable for making a plastic product. In the context of the invention, the plastic compound encompasses homogeneous blends of at least one polyester and at least one polypeptide and/or recombinant cell expressing the polypeptide of the invention, wherein said polypeptide and/or recombinant cell is able to degrade said polyester. Preferably, the plastic compound is constituted of a mix of semi-crystalline and/or amorphous polymers, or semi-crystalline polymers and additives.

In the present description, "polyesters" encompass polyethylene terephthalate (PET), polytrimethylene terephthalate (PTT), polybutylene terephthalate (PBT), polyethylene isosorbide terephthalate (PEIT), polylactic acid (PLA), poly (L-lactic acid) (PLLA), poly(D-lactic acid) (PDLA), poly (D,L-lactic acid) (PDLLA), PLA stereocomplex (scPLA), polyhydroxy alkanoate (PHA), Poly(3-hydroxybutyrate) (P(3HB)/PHB), Poly(3-hydroxyvalérate) (P(3HV)/PHV), Poly(3-hydroxyhexanoate) (P(3HHx)), Poly(3-hydroxyoctanoate) (P(3HO)), Poly(3-hydroxydecanoate) (P(3HD)), Poly(3-hydroxybutyrate-co-3-hydroxyvalerate) (P(3HB-co-3HV)/PHBV), Poly(3-hydroxybutyrate-co-3-hydroxyhexanoate) (P(3HB-co-3HHx)/(PHBHHx)), Poly(3-hydroxybutyrate-co-5-hydroxyvalerate) (PHB5HV), Poly(3-hydroxybutyrate-co-3-hydroxypropionate) (PHB3HP), Polyhydroxybutyrate-co-hydroxyoctonoate (PHBO), polyhydroxybutyrate-co-hydroxyoctadecanoate (PHBOd), Poly (3-hydroxybutyrate-co-3-hydroxyvalerate-co-4-hydroxybutyrate) (P(3HB-co-3HV-co-4HB)), polybutylene succinate (PBS), polybutylene succinate adipate (PBSA), polybutylene adipate terephthalate (PBAT), polyethylene furanoate (PEF), Polycaprolactone (PCL), poly(ethylene adipate) (PEA) and blends/mixtures of these polymers.

A "polymer" refers to a chemical compound or mixture of compounds whose structure is constituted of multiple repeating units linked by covalent chemical bonds. Within the context of the invention, the term polymer includes natural or synthetic polymers, constituting of a single type of repeat unit (i.e., homopolymers) or of a mixture of different repeat units (i.e., copolymers).

According to the invention, "oligomers" refer to molecules containing from 2 to about 20 monomer units.

New Isolated Polypeptide

The present invention is directed to a new polypeptide having the ability to degrade plastics having ester bonds in their molecular structure. More particularly, the present invention discloses a newly identified and isolated polypeptide that exhibits a polyesterase activity. Said polypeptide was originally isolated from natural bacterial strains of *Actinomadura keratinilytica* T16-1 or DSMZ 45195. Interestingly, the polypeptide of the invention is capable of hydrolyzing ester bonds in natural and man-made polyesters.

In a first aspect, the present invention relates to an isolated polypeptide comprising an amino acid sequence having at least 94%, 95%, 99% or 100% identity to the full length amino acid sequence set forth in SEQ ID NO: 1, provided below, and having a polyester degrading activity.

Advantageously, the polypeptide comprises an amino acid sequence having at least 95%, 96%, 97%, 98%, 99% or 100% identity to the full length amino acid sequence set forth in SEQ ID NO: 1.

```
SEQ ID NO: 1:
ATQNNPPSWGLDRIDQTNLPLSRSYTYNSTGAGVNAYIIDTGIYTAHSDF

GGRATNVYDALGGNGQDCNGHGTHVAGTVGGAAYGVAKAVNLRGVRVLNC

SGSGTTSGVIAGMNWVASNHVKPAVANMSLGGGYSSSLNTAANNLASSGV

FLAVAAGNETTNACNRSPASAANATTVAASTSTDARASYSNYGSCVHLYA

PGSSITSAWLNGGTNTISGTSMATPHVAGTAALYKATYGDASFSTIRSWL

VSNATSGVITGNVSGTPNLLLNKRSL
```

As used herein, the polypeptide of the invention may also be referred to as a polypeptide having a polyesterase activity or, interchangeably, as a polyesterase.

It is a particular object of the invention to provide an isolated polypeptide comprising an amino acid sequence having at least 94%, 95%, 99% or 100% identity to the full length amino acid sequence set forth in SEQ ID NO: 1, and having a polylactic acid degrading activity, and more preferably a poly-(L-lactic) acid degrading activity. In a particular embodiment, the polypeptide comprises an amino acid sequence having at least 94%, 95%, 96%, 97%, 98%, 99% or 100% identity to the full length amino acid sequence set forth in SEQ ID NO: 1.

In a particular embodiment, the isolated polypeptide comprises all or a biologically active part of the amino acid sequence set forth in SEQ ID NO: 1. A "biologically active part" of the polypeptide more specifically designates a portion of that polypeptide which confers or exhibits the polyesterase activity of the entire polypeptide. The active part may, for instance, confer substrate specificity or affinity, it may contain the catalytic site. An active part of the polypeptide also designates a mature form of the polypeptide (i.e., that does not contain a signal peptide at the N-terminal end of the polypeptide). In an embodiment, the biologically active part comprises at least a portion of the amino acid sequence set forth in SEQ ID NO: 1, including the amino acids His 71, Asp 40 and Ser 221 forming the catalytic site of the polypeptide. Alternatively, or in addition, the active part advantageously comprises the amino acids Ala 172, Ala 174 and His 197 and/or the amino acids Asp 12, Asp 15 and Gln 16 that form calcium binding sites and/or the amino acids Cys 68-Cys 100 and Cys 164-Cys 195 that form disulfide bond and/or amino acids forming the polyester binding site. In a particular embodiment, the biologically active part comprises or is constituted of the amino acids 12 to 221 of SEQ ID NO: 1. In another embodiment, the biologically active part comprises or is constituted of the amino acids 40 to 221 of SEQ ID NO: 1.

It is a further object of the invention to provide a polypeptide comprising or consisting of the amino acid sequence set forth in SEQ ID NO: 1 or SEQ ID NO: 5. It is a further object of the invention to provide a peptide comprising or constituted of the amino acids 1 to 29 of SEQ ID NO: 5, corresponding to the peptide signal of the polypeptide.

```
SEQ ID NO: 5:
MRRRTLPIAVLAAVPLAVAGALPAGAAPAAPAVPVAMAAAGQGVAGQYIV

TLKKGVSVDSTVAKRGIRTQHRFGKVLNGFSAKLTDDQLSKLRTTPGVAS

IEQDAVITVDATQNNPPSWGLDRIDQTNLPLSRSYTYNSTGAGVNAYIID

TGIYTAHSDFGGRATNVYDALGGNGQDCNGHGTHVAGTVGGAAYGVAKAV

NLRGVRVLNCSGSGTTSGVIAGMNWVASNHVKPAVANMSLGGGYSSSLNT

AANNLASSGVFLAVAAGNETTNACNRSPASAANATTVAASTSTDARASYS

NYGSCVHLYAPGSSITSAWLNGGTNTISGTSMATPHVAGTAALYKATYGD

ASFSTIRSWLVSNATSGVITGNVSGTPNLLLNKRSL
```

It is another object of the invention to provide a variant of the polypeptide as set forth in SEQ ID NO: 1, comprising a substitution, deletion and/or insertion of one or several amino acid residues of the polypeptide of SEQ ID NO: 1, having a polyester degrading activity.

In a particular embodiment, the variant exhibits a greater thermostability compared to the native polypeptide. For instance, disulphide bonds are introduced by substitutions and/or insertions of amino acid residues, leading to additional cysteine residues in the amino acid sequence compared to the native one. Alternatively or in addition, extra salt bridges may be introduced in the amino acid sequence of the polypeptide.

In a particular embodiment, the variant comprises one or several substitutions relative to SEQ ID NO: 1, selected from T175C, R247C, N139D, S170R, N143R, N173E, S194P, H197D, L210P, G212N, I217K, R166K, T160A, L138A or combinations thereof, and has a polyester degrading activity, preferably a PLA degrading activity.

In a particular embodiment, the variant comprises or consists on the amino acid sequence of SEQ ID NO: 1 with the substitutions T175C and R247C, and has a polyester degrading activity, preferably a PLA degrading activity.

In another particular embodiment, the variant comprises or consists on the amino acid sequence of SEQ ID NO: 1 with the substitutions N139D and S170R, and has a polyester degrading activity, preferably a PLA degrading activity.

In a further particular embodiment, the variant comprises or consists on the amino acid sequence of SEQ ID NO: 1 with the substitutions N143R and N173E, and has a polyester degrading activity, preferably a PLA degrading activity.

In a particular embodiment, the variant comprises or consists on the amino acid sequence of SEQ ID NO: 1 with the substitutions T175C, R247C, N139D, S170R, N143R, N173E, S194P, H197D, L210P, G212N, I217K, R166K, T160A and L138A, and has a polyester degrading activity, preferably a PLA degrading activity.

In a particular embodiment, the variant comprises at most 14 amino acid residue substitutions compared to the amino acid sequence set forth in SEQ ID NO: 1, and has a polyester degrading activity, preferably a PLA degrading activity. In another embodiment, the variant comprises at most 17 amino acid residue substitutions compared to the amino acid sequence set forth in SEQ ID NO: 1.

Advantageously, the variant has a better polyester degrading activity than the native polypeptide of SEQ ID NO: 1. More preferably, the variant polypeptide has a greater stability at high temperatures than the native polypeptide of SEQ ID NO: 1.

In another embodiment, the polypeptide comprises one or several glycosylations. For instance, the polypeptide comprises the amino acid sequence set forth in SEQ ID NO: 1, wherein at least one amino acid residue is glycosylated. Advantageously, such glycosylated polypeptide shows a greater stability compared to the native polypeptide (unglycosylated polypeptide of SEQ ID NO: 1), specifically a greater thermostability. For instance, at least one asparagine residue of the amino acid sequence of SEQ ID NO: 1 is glycosylated and an oligosaccharide is linked at the amide nitrogen of said asparagine residue. More particularly, the SEQ ID NO: 1 comprises at least one glycosylation of one amino acid residues selected from: N28, N99, N127, N158, N165, N173, N253, N262 or combinations thereof. In a preferred embodiment, the SEQ ID NO: 1 comprises at least one glycosylation of one amino acid residues selected from: N28, N158, N165.

The polypeptide of the invention is particularly active in a range of temperatures from 20° C. to 90° C., preferably from 20° C. to 60° C., more preferably from 30° C. to 55° C., even more preferably from 40° C. to 50° C., even more preferably at 45° C. In a particular embodiment, the polypeptide is still active at a temperature between 60° C. and 90° C., preferably at 80° C.

Similarly, the polypeptide of the invention is particularly active in a range of pH from 5 to 11, preferably in a range of pH from 7 to 10, more preferably in a range of pH from 8.5 to 9.5, even more preferably in a range of pH from 8 to 9.

The isolated polypeptide of the invention advantageously has a productivity of at least 0.02 $g \cdot mg^{-1} \cdot h^{-1}$, 0.05 $g \cdot mg^{-1} \cdot h^{-1}$, 0.1 $g \cdot mg^{-1} \cdot h^{-1}$, 0.15 $g \cdot mg^{-1} \cdot h^{-1}$, 0.2 $g \cdot mg^{-1} \cdot h^{-1}$, 0.5 $g \cdot mg^{-1} \cdot h^{-1}$, 1 $g \cdot mg^{-1} \cdot h^{-1}$, 1.5 $g \cdot mg^{-1} \cdot h^{-1}$ or 2 $g \cdot mg^{-1} \cdot h^{-1}$. By "productivity" is meant the amount of product of degradation (i.e., monomers) formed per unit of polypeptide and per unit time, at a pH comprised between 8 and 9 and at a temperature of 45° C.+/−5° C.

The polypeptide of the invention is particularly useful for degrading polylactic acid (PLA), and more particularly poly(L-lactic acid) (PLLA).

In a particular embodiment, the polypeptide of the invention is enantiospecific. This means that the polypeptide is capable of acting on L-enantiomer in a polyester while being inefficient on D-enantiomer, or the reverse.

The polypeptide of the invention may be produced by recombinant techniques, or it may be isolated or purified from natural sources (i.e., microorganisms and more particularly bacteria, yeasts or fungi), or it may be artificially produced. Within the context of the invention, the term "derived from a microorganism" in relation to a polypeptide indicates that the polypeptide has been isolated from such a microorganism, or that the polypeptide comprises all or a biologically active part of the amino acid sequence of a polypeptide isolated or characterized from such a microorganism. More particularly, the polypeptide of the invention may be produced by recombinant *Bacillus*, recombinant *E. Coli* or recombinant *Yarrowia lipolytica*.

The polypeptide of the invention may be purified by techniques known per se in the art such as chromatography (e.g. ion exchange, affinity, size-exclusion, reversed-phase, etc.) and precipitation (e.g. salt-out, isoelectric point, organic solvents, non-ionic hydrophilic polymers, etc.), and stored under conventional techniques. The polypeptide may be further modified to improve e.g., its stability or activity. It may be used as such, in purified form, either alone or in combinations with additional enzymes, to catalyze enzymatic reactions involved in the degradation and/or recycling of a polyester containing material. The polypeptide may be in soluble form, or on solid phase. In particular, it may be bound to cell membranes or lipid vesicles, or to synthetic supports such as glass, plastic, polymers, filter, membranes, e.g., in the form of beads, columns, plates and the like.

It is a further object of the invention to provide a composition comprising the isolated polypeptide of the invention and/or corresponding nucleic acid, expression cassette, vector, recombinant cell or recombinant cell extract, and optionally additives, excipients etc. In the context of the invention, the term "composition" encompasses all kind of compositions comprising the polypeptide of the invention in isolated or at least partially purified form. The composition may be liquid or dry, for instance in the form of a powder. In some embodiments, the composition is a lyophilisate. For instance, the composition may comprise the polypeptide and/or recombinant cells encoding the polypeptide of the invention or extract thereof, and optionally excipients and/or reagents etc. Appropriate excipients encompass buffers commonly used in biochemistry, agents for adjusting pH, preservatives such as sodium benzoate, sodium sorbate or sodium ascorbate, conservatives, protective or stabilizing agents such as starch, dextrin, arabic gum, salts, sugars e.g. sorbitol, trehalose or lactose, glycerol, polyethyleneglycol, polyethene glycol, polypropylene glycol, propylene glycol, sequestering agent such as EDTA, amino acids, a carrier such as a solvent or an aqueous solution, and the like. The composition of the invention may be obtained by mixing the polypeptide with one or several excipients.

The composition of the invention may comprises from 0.1% to 90%, preferably from 0.1% to 50%, more preferably from 0.1% to 30%, even more preferably from 0.1% to 5% by weight of the polypeptide of the invention and from 10% to 99.9%, preferably from 50% to 99.9%, more preferably from 30% to 99.9%, even more preferably from 95% to 99.9% by weight of excipient(s). A preferred composition comprises between 0.1 and 5% by weight of the polypeptide of the invention.

In a particular embodiment, the composition may further comprise additional polypeptide(s) exhibiting an enzymatic activity. The amounts of polypeptide of the invention will be easily adapted by those skilled in the art depending e.g., on the nature of the polyester containing material to degrade and/or the additional enzymes/polypeptides contained in the composition.

In a particular embodiment, the isolated polypeptide of the invention is solubilized in an aqueous medium together with one or several excipients, especially excipients which are able to stabilize or protect the polypeptide from degradation. For instance, the polypeptide of the invention may be solubilized in water, eventually with additional components, such as glycerol, sorbitol, dextrin, starch, glycol such as propanediol, salt, etc. The resulting mixture may then be dried so as to obtain a powder. Methods for drying such mixture are well known to the one skilled in the art and include, without limitation, lyophilisation, freeze-drying, spray-drying, supercritical drying, down-draught evaporation, thin-layer evaporation, centrifugal evaporation, conveyer drying, fluidized bed drying, drum drying or any combination thereof.

In a further particular embodiment, the composition of the invention comprises at least one recombinant cell expressing the polypeptide of the invention, or an extract thereof. An "extract of a cell" designates any fraction obtained from a cell, such as a cell supernatant, cell debris, cell walls, DNA extract, enzymes or enzyme preparation or any preparation derived from cells by chemical, physical and/or enzymatic treatment, which is essentially free of living cells. Preferred extracts are enzymatically-active extracts. The composition of the invention may comprise one or several recombinant cells of the invention or extract thereof, and optionally one or several additional cells.

In a particular embodiment, the composition consists or comprises a lyophilized culture medium of a recombinant microorganism expressing and excreting the polypeptide of the invention. In a particular embodiment, the powder comprises the polypeptide of the invention and a stabilizing/solubilizing amount of glycerol, sorbitol or dextrin, such as maltodextrine and/or cyclodextrine, starch, glycol such as propanediol, and/or salt.

In a further embodiment, the polypeptide of the invention is immobilized on a solid support. The polypeptide may be immobilized by any appropriate method described in the state in the art, for instance, covalent binding, adsorption, entrapment or membrane confinement. A wide variety of supports may be used for immobilizing the polypeptide of the invention. The support to select depends on its dedicated use. Convenient supports encompass, without being limited to, plastic, metal, inorganic support such as glass, silica, alumina, bentonite, hydroxyapatite, nickel/nickel oxide, titanium, zirconia, polymeric supports and the like. The support may be in the form of a surface, a powder, micro- or nanobeads, a gel, a solvent-swelling or water-swelling gel or matrix, a reticulated matrix or gel, a membrane, a fibrous support, a porous support and the like. The methods for immobilizing the polypeptide are well-known to the skilled artisan (see for instance, Tischer and Wedekind, Topics in Current Chemistry, 1999, 200, 95-126 and Alloue et al, Biotechnol Agron Soc Environ 2008, 12, 57-68; the disclosure thereof being incorporated herein by reference).

Once prepared, the support of the invention can be directly used in a reaction medium. In other words, the support of the invention may be merely added in the reaction medium. When the support is solvent-swelling, the solvent of the reaction may be selected so as to provide an appropriate swelling of the support to render accessible the immobilized polypeptide without impairing the catalytic activity of the polypeptide. As an alternative, the support can be used to prepare a reactor, which can be for instance an enzyme reactor, a membrane reactor, a continuous flow reactor such as a stirred tank reactor, a continuously operated packed bed reactor, or a continuously operated fluidized bed reactor, or a packed bed reactor. In some embodiments, the support of the invention is recyclable and may be used several times in a row.

Nucleic Acids

A further object of the invention is a nucleic acid encoding a polypeptide as defined above.

As used herein, the term "nucleic acid", "nucleic sequence," "polynucleotide", "oligonucleotide" and "nucleotide sequence" are used interchangeably and refer to a sequence of deoxyribonucleotides and/or ribonucleotides. The nucleic acids can be DNA (cDNA or gDNA), RNA, or a mixture of the two. It can be in single stranded form or in duplex form or a mixture of the two. It can be of recombinant, artificial and/or synthetic origin and it can comprise modified nucleotides, comprising for example a modified bond, a modified purine or pyrimidine base, or a modified sugar.

The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding the polypeptide as defined above. Preferably, such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding the polypeptide of the invention, wherein the sequence of said nucleic acids, or a portion of said sequence at least, has been engineered using optimized codon usage.

A specific embodiment of this invention resides in an isolated nucleic acid encoding a polypeptide as defined above, comprising the sequence set forth in SEQ ID NO: 2, as disclosed below.

```
SEQ ID NO: 2:
5'gccacgcagaacaacccgccgtcgtggggcctggaccgcatcgaccag acgaacctgccgctgtcgcgcagctacacctacaattccaccggcgcggg cgtgaacgcctacatcatcgacaccggcatctacaccgcgcactccgact tcggcggccgcgccaccaacgtctacgacgccctcggcggcaacggccag gactgcaacggccacggcacccacgtcgcgggcaccgtcggcggcgccgc ctacggcgtggccaaggcggtcaacctgcgcggcgtgcgcgtgctcaact gcagcggcagcggcaccacctccggtgtcatcgccggcatgaactgggtg gccagcaaccacgtcaagcccgccgtggcgaacatgtcgctgggcggcgg ctactcctcctccctgaacacggccgccaacaacctggccagctccggcg tgttcctggccgtcgccgcgggcaacgagaccaccaacgcctgcaaccgc tcgccggccagcgccgccaacgccaccacggtcgccgcgagcaccagcac cgacgcccgggcctcctacagcaactacggctcgtgcgtccacctgtacg cgcccggctcgtccatcacctccgcctggctgaacggcggcaccaacacc atcagcggcacgtcgatggccacgccgcacgtggccgggaccgccgccct ctacaaggcgacctacggcgacgcctcgttcagcaccatccgcagctggc
```

-continued

```
tggtcagcaacgccacctccggcgtcatcaccggcaacgtgtcgggcacc ccgaacctgctgctgaacaagcgctccctg 3'
```

Alternatively, the nucleic acids according to the invention may be deduced from the sequence of the polypeptide according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

Nucleic acids of this invention may further comprise additional nucleotide sequences, such as regulatory regions, i.e., promoters, enhancers, silencers, terminators, signal peptides and the like that can be used to cause or regulate expression of the polypeptide in a selected host cell or system.

The present invention further relates to an expression cassette comprising a nucleic acid according to the invention operably linked to one or more control sequences that direct the expression of said nucleic acid in a suitable host cell. Typically, the expression cassette comprises, or consists of, a nucleic acid according to the invention operably linked to a transcriptional promoter and a transcription terminator.

The invention also relates to a vector comprising a nucleic acid or an expression cassette as defined above.

The term "vector" refers to DNA molecule used as a vehicle to transfer recombinant genetic material into a host cell. The major types of vectors are plasmids, bacteriophages, viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. Generally, the regulatory elements that are present in an expression vector include a transcriptional promoter, a ribosome binding site, a terminator, and optionally present operator. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. Bacterial expression vectors well known in the art include pET11a (Novagen), lamda gt11 (Invitrogen).

The present invention further relates to the use of a nucleic acid, expression cassette or vector according to the invention to transform, transfect or transduce a host cell. The choice of the vector will typically depend on the compatibility of the vector with the host cell into which the vector is to be introduced.

The present invention also relates to a host cell, or recombinant cell, comprising a nucleic acid, cassette or vector according to the invention. The host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The expression cassette or vector may be introduced into host cells using standard techniques. Examples of such techniques include transformation, transfection, lipotransfection, protoplast fusion, and electroporation.

The host cell may be any cell that can be genetically modified and, preferably, cultivated. The cell can be eukaryotic or prokaryotic, such as a mammalian cell, an insect cell, a plant cell, a microorganism such as yeast, fungus or bacterial cell, etc. In a particular embodiment, the host cell is selected from the group of *Escherischia Coli, Bacillus*, Lactic acid bacteria, *Streptomyces, Trichoderma, Aspergillus, Pichia* or *Yarrowia*. It should be understood that the invention is not limited with respect to any particular cell type, and can be applied to all kinds of cells, following common general knowledge. The term "host cell" also encompasses any progeny of a parent host cell that is not identical to the parent host cell due to mutations that occur during replication.

In a particular embodiment, the host cell is a yeast, preferably *Yarrowia*, and the polypeptide produced is a glycosylated polypeptide showing a greater thermostability. In a preferred embodiment, the polypeptide consists of the SEQ ID NO: 1 comprising at least one glycosylation of one amino acid residues selected from N28, N158, or N165.

In a particular embodiment, the present invention provides a host cell engineered to express the nucleic acids set forth in SEQ ID NO: 2 or expression cassette thereof.

In a particular embodiment, the invention provides a recombinant *Bacillus subtilis* engineered to express the nucleic acids set forth in SEQ ID NO: 2 or expression cassette thereof.

In another particular embodiment, the invention provides a recombinant *E. coli* engineered to express the nucleic acids set forth in SEQ ID NO: 2 or expression cassette thereof.

In a further particular embodiment, the invention provides a recombinant *Yarrowia lipolytica* engineered to express the nucleic acids set forth in SEQ ID NO: 2 or expression cassette thereof.

In a further embodiment, the present invention provides a host cell comprising and expressing a nucleotide sequence encoding a polypeptide comprising an amino acid sequence having at least 94%, 95%, 99% or 100% identity to the full length amino acid sequence set forth in SEQ ID NO: 1, and having a polyester degrading activity.

In another embodiment, the present invention provides a host cell comprising and expressing a nucleotide sequence encoding a polypeptide comprising an amino acid sequence having at least 94%, 95%, 99% or 100% identity to the full length amino acid sequence set forth in SEQ ID NO: 1, and having a PLA degrading activity, more preferably a PLLA degrading activity.

In a particular embodiment, the host cell is a recombinant microorganism. The invention indeed allows the engineering of microorganisms with improved capacity to degrade polyester containing material. For instance, the sequence of the invention may be used to complement a wild type strain of a fungus or bacterium already known as able to degrade polyester, in order to improve and/or increase the strain capacity.

In a particular embodiment, the invention provides a recombinant *Bacillus subtilis* comprising and expressing a nucleotide sequence encoding a polypeptide comprising an amino acid sequence having at least 94%, 95%, 96%, 97%, 98%, 99% or 100% identity to the full length amino acid sequence set forth in SEQ ID NO: 1, and having a polyester degrading activity, preferably a PLA degrading activity, more preferably a PLLA degrading activity.

In another particular embodiment, the invention provides a recombinant *E. coli* comprising and expressing a nucleotide sequence encoding a polypeptide comprising an amino acid sequence having at least 94%, 95%, 96%, 97%, 98%, 99% or 100% identity to the full length amino acid sequence set forth in SEQ ID NO: 1, and having a polyester degrading activity, preferably a PLA degrading activity, more preferably a PLLA degrading activity.

In a further particular embodiment, the invention provides a recombinant *Yarrowia lipolytica* comprising and expressing a nucleotide sequence encoding a polypeptide comprising an amino acid sequence having at least 94%, 95%, 96%, 97%, 98%, 99% or 100% identity to the full length amino acid sequence set forth in SEQ ID NO: 1, and having a polyester degrading activity, preferably a PLA degrading activity, more preferably a PLLA degrading activity. Advantageously, one or several amino acid residues of the polypeptide are glycosylated. More preferably, the polypeptide consists of the SEQ ID NO: 1 comprising at least one glycosylation of one amino acid residues selected from N28, N158, or N165, preferably at least N158.

It is a further object of the invention to provide a method of producing a polypeptide of the invention, comprising (i) culturing a recombinant cell as defined above, (ii) recovering the culture supernatant, and optionally (iii) isolating or purifying the polypeptide. The invention further relates to such polypeptide obtained by this method of production.

Alternatively, the polypeptide of the invention may be produced via cell free methods (Kim et al. J Biosci. Bioeng. July 2009; Spirin et al. (2007) Front Matter in Cell-Free Protein Synthesis: Methods and Protocols) or may be chemically synthesized.

Degradation of Polyester Containing Material

The present invention provides methods using the polypeptide of the invention for degradation in aerobic or anaerobic conditions and/or recycling of polyester containing material, as plastic products made or containing polyesters. Indeed, due to its high polyester depolymerizing efficiency, the polypeptide of the invention is much more advantageous in comparison with other known chemical or microbial polyester degradation means. The polypeptide of the invention has an increased depolymerizing rate, in particular for PLA depolymerization.

It is therefore an object of the invention to use the polypeptide of the invention, or corresponding recombinant cell or extract thereof, or composition for the enzymatic degradation of a polyester containing material. In a preferred embodiment, the polypeptide, or corresponding recombinant cell, extract thereof, or composition is used for the enzymatic degradation of a PLA containing material, and more preferably for the enzymatic degradation of a PLLA containing material.

It is another object of the invention to use a polypeptide comprising an amino acid sequence having at least 75%, 80%, 85%, 90%, 95%, 99% or 100% identity to the full length amino acid sequence set forth in SEQ ID NO: 1, and having a polyester degrading activity for degrading a polyester containing material.

It is another object of the invention to provide a method for degrading a polyester containing material, wherein a polyester containing material is contacted with the polypeptide of the invention, or corresponding recombinant cell or extract thereof, or composition. Advantageously, polyester(s) of the polyester containing material is (are) depolymerized up to monomers and/or oligomers. In a particular embodiment, all the targeted polyesters are depolymerized up to the monomers that formed the original polyesters of the material.

In an embodiment of the degradation process, at least one polyester is degraded to yield repolymerizable monomers and/or oligomers, which are advantageously retrieved in order to be reused.

In another embodiment, polyester(s) of the polyester containing material is(are) fully degraded.

In a preferred embodiment, the polyester containing material comprises PLA, more preferably PLLA, and at least lactic acid monomers and/or oligomers are recovered for recycling or methanisation for instance.

In a further embodiment, the polyester containing material comprises PLA and at least one additional polyester, preferably selected from polytrimethylene terephthalate (PTT), polybutylene terephthalate (PBT), polyethylene terephthalate (PET), polybutylene adipate terephthalate (PBAT), polyhydroxyalkanoate (PHA), polybutylene succinate (PBS), polycaprolactone (PCL), poly(ethylene adipate) (PEA), and blends/mixtures of these polyesters.

Alternatively or in addition, the polyester containing material may further contain at least one polyamide (also called nylon) and/or at least one polyolefin, preferably selected from the group consisting of polyethylene (PE), polypropylene (PP), and blends/mixtures of these polymers, and/or at least one vinyl polymer made from vinyl monomers, small molecules containing carbon-carbon double bonds.

Alternatively or in addition, the polyester containing material may further contain at least one natural polymer (i.e., non petrochemically derivated), preferably selected from starch, flour, cellulose, and blends/mixtures thereof.

In a particular embodiment, the polyester containing material comprises polyhydroxyalkanoate (PHA) and/or polyethylene terephthalate (PET) and/or polybutylene adipate terephthalate (PBAT), or blends/mixtures of these polyesters.

According to the invention, the polyester containing material may also contain metal compounds, mineral compounds, glass compounds, natural or synthetic fibers, paper, wood, wood compounds as lignin, cellulose or hemi-cellulose, starch, and derivatives thereof.

The invention also relates to a method of producing monomers and/or oligomers from a polyester containing material, comprising exposing a polyester containing material to the polypeptide of the invention, or corresponding recombinant cell or extract thereof, or composition, and optionally recovering monomers and/or oligomers. The method of the invention is particularly useful for producing lactic acid monomers.

When a recombinant microorganism is used, such microorganism advantageously exhibits a modified metabolism in order to prevent the consumption of the monomers and/or oligomers obtained from the degraded polyester. For example, the enzymes degrading said monomers and/or oligomers have been deleted or knocked out in the microorganism. Alternatively, the method of the invention may be performed in a culture medium containing at least one carbon source usable by the recombinant microorganism so that said microorganism preferentially consumes this carbon source instead of the monomers and/or oligomers. Advantageously, the polyester containing material is contacted with a culture medium containing the recombinant microorganisms, glucose or the like as a carbon source, as well as an available nitrogen source, including an organic nitrogen source (e.g., peptone, meat extract, yeast extract, corn steep liquor) or an inorganic nitrogen source (e.g., ammonium sulfate, ammonium chloride). If necessary, the culture medium may further contain inorganic salts (e.g., sodium ion, potassium ion, calcium ion, magnesium ion, sulfate ion, chlorine ion, phosphate ion). Moreover, the medium may also be supplemented with trace components such as vitamins, oligo-elements and amino acids.

In a particular embodiment, the polyester containing material may be pretreated prior to be contacted with the polyesterase of the invention, in order to physically change its structure, so as to increase the surface of contact between the polyesters and the polyesterase. For example, the polyester containing material may be transformed to an emulsion or a powder, which is added to a liquid medium containing the polypeptide of the invention and/or recombinant microorganism or extract thereof. Alternatively, the polyester containing material may be mechanically ground, granulated, pelleted, etc. by cutting, impact, crushing, grinding, fractionation, cryogenic grinding, or the like, to reduce the shape and size of the material prior to be added to a liquid medium containing the recombinant microorganism, extract thereof and/or polypeptide. The mechanical pretreatment can also be a sonication, a centrifugation, a shear, a collisop, a high-pressure homogenizer, a maceration or a liquefaction with a rotary drum, a screw press, a disc screen shredder, or a piston press. Alternatively or additionally, a thermal pretreatment can be applied. It can be achieved with microwaves. Such thermal pretreatment may provide disinfection, pasteurization or sterilization. In another embodiment, the polyester containing material is chemically pretreated to modify its structure and increase the surface of contact between the polyesters and the polypeptide of the invention. A base, an acid, a solvent or an ionic liquid can be used. An ozonation can also be implemented. In a particular embodiment, the polyester containing material may also be sorted, washed, disinfected, sterilized and/or biologically cleaned prior to degradation. According to the invention, several pre-treatments may be combined.

The time required for degradation of a polyester containing material may vary depending on the polyester containing material itself (i.e., nature and origin of the plastic product, its composition, shape etc.), the type and amount of polypeptide used, as well as various process parameters (i.e., temperature, pH, additional agents, etc.). One skilled in the art may easily adapt the process parameters to the polyester containing material.

Advantageously, the process is implemented at a temperature comprised between 20° C. and 90° C., preferably between 20° C. and 60° C., more preferably between 30° C. and 55° C., more preferably from 40° C. to 50° C., even more preferably at 45° C. More generally, the temperature is maintained below an inactivating temperature, which corresponds to the temperature at which the polypeptide is inactivated and/or the recombinant microorganism does no more synthesize the polypeptide.

The pH of the medium may be in a range of pH from 5-11, preferably in a range of pH from 7-10, more preferably in a range of pH from 8.5-9.5, even more preferably in a range of pH from 8-9. Advantageously, the pH is adjusted according to the targeted polyester and the solubility of the targeted monomers/oligomers for improving the process efficiency. Preferably, the pH is adjusted to be maintained at the optimal pH of the polypeptide. Indeed, depolymerization of polyesters produces acidic monomers and oligomers that induce a pH decrease. An addition of a diluted alkali or saturated alkali, such as calcium hydroxyde can be used to compensate this acidification and maintain the pH to the optimal one.

Advantageously, the added amount of polypeptide is in a range of 0.001% to 5% by weight of polyester containing material, preferably in a range of 0.001% to 1%, more preferably in a range of 0.001% to 0.1%, even more preferably in a range of 0.001% to 0.05%.

In a particular embodiment, the process is performed under agitation, preferably comprised between 30 rpm and 2000 rpm, in order to favor contact between the polypeptide and the polyester containing material.

In a particular embodiment, at least a lipophilic agent and/or hydrophilic agent is added to the medium for improving the depolymerization step. An inductor such as oligomers of polyesters or derivatives thereof can be added to the medium comprising recombinant microorganism to improve polypeptide production. A surfactant such as Tween or a small protein like hydrophobin can be added to the medium to modify interface energy between the polyester and the polypeptide or recombinant microorganism and improve degradation efficiency. An organic substance or an ionic liquid could be used to swell the polyester and increase its accessibility to the microorganism or polypeptide.

The reaction time for depolymerization of at least one polyester of the plastic material up to monomers/oligomers is advantageously comprised between 5 or less and 110 hours, more preferably between 24 and 72 hours. Such reaction time may allow the depolymerization to advance sufficiently, and will not be economically detrimental. The reaction time can be longer for anaerobic biodegradation in a methanisation site or for aerobic biodegradation in natural environment.

Optionally, monomers and/or oligomers resulting from the depolymerization may be recovered, sequentially or continuously. A single type of monomers and/or oligomers or several different types of monomers and/or oligomers may be recovered, depending on the starting polyester containing material.

The recovered monomers and/or oligomers may be further purified, using all suitable purifying method and conditioned in a re-polymerizable form. Examples of purifying methods include stripping process, separation by aqueous solution, steam selective condensation, filtration and concentration of the medium after the bioprocess, separation, distillation, vacuum evaporation, extraction, electrodialysis, adsorption, ion exchange, precipitation, crystallization, concentration and acid addition dehydration and precipitation, nanofiltration, acid catalyst treatment, semi continuous mode distillation or continuous mode distillation, solvent extraction, evaporative concentration, evaporative crystallization, liquid/liquid extraction, hydrogenation, azeotropic distillation process, adsorption, column chromatography, simple vacuum distillation and microfiltration, combined or not.

The repolymerizable monomers and/or oligomers may then be reused for instance to synthesize polyesters. Advantageously, polyesters of same nature are repolymerized. However, it is possible to mix the recovered monomers and/or oligomers with other monomers and/or oligomers, in order for instance to synthesize new copolymers. Alternatively, the recovered monomers may be used as chemical intermediates in order to produce new chemical compounds of interest.

In a particular embodiment, repolymerization is conducted using a hydrolase in appropriate conditions for allowing polymerization reaction. Initiators may be added to the monomers/oligomers solution to favour the polymerization reaction. One skilled in the art may easily adapt the process parameters to the monomers/oligomers and the polymers to synthesize.

In a particular embodiment, the methods of the invention are performed in a reactor. "Reactor" designates any device or installation or facility suitable for maintaining and transforming plastic articles. A reactor may comprise inlet and outlet devices to supply/collect medium, nutrients, gas, etc. The reactor may be closed or open, such as a tank.

Plastic Compound and Article

It is a further object of the invention to provide a polyester containing material in which the polypeptide of the invention and/or a recombinant microorganism expressing and excreting said polypeptide is/are included. In a particular embodiment, such polyester containing material may be a plastic compound.

It is thus an object of the invention to provide a plastic compound containing the polypeptide of the invention and/or a recombinant cell and/or a composition or extract thereof; and at least one polyester. In a preferred embodiment, the polyester is selected from polylactic acid, preferably from PLLA. Particularly, the plastic compound may contain an additional polymer, preferably selected from polyesters such as PDLA, PBAT, PHA, PCL, PET; polyolefins such as polyethylene, polypropylene or natural polymers such as starch, cellulose or flour; and blends/mixtures thereof. More particularly, the plastic compound may contain additional polymers selected from PBAT and flour or starch.

In a particular embodiment, the polypeptide used for preparing the plastic compound comprises an amino acid sequence having at least 75%, 80%, 85%, 90%, 92%, 95%, 99% or 100% identity to the full length amino acid sequence set forth in SEQ ID NO: 1.

In particular, the invention relates to a process comprising a step of mixing a polyester and a polypeptide and/or the recombinant cell of the invention that degrade said polyester, at a temperature at which the polyester is in a partially or totally molten state so that the polypeptide and/or the recombinant cell are integrated into the very structure of the polyester containing material. In a particular embodiment, spores of a recombinant microorganism are included into the polyester containing material.

For instance, the polypeptide and/or the recombinant microorganism of the invention and the polyester may be mixed at a temperature between the glass transition temperature and the melting point of the polyester. Alternatively, the biological entity and the polyolefin may be mixed at a temperature corresponding to the melting point of said polyester, or above. In a particular embodiment, the polypeptide/microorganism and polyester are mixed at a temperature between 80° C. and 250° C., preferably between 100° C. and 200° C. Alternatively, the polypeptide/microorganism and polyester are mixed at a temperature above 80° C., preferably, above 100° C., even more preferably above 130° C. More generally, the polypeptide and/or the recombinant microorganism advantageously resists at least to the temperature of extrusion of the polyester.

More preferably, the mixing step is performed using extrusion, twin screw extrusion, single screw extrusion, injection-molding, casting, thermoforming, rotary molding, compression, calendering, ironing, coating, stratification, expansion, pultrusion, extrusion blow-molding, extrusion-swelling, compression-granulation, water-in-oil-in-water double emulsion evaporation or any techniques known by person skilled in the art.

The resulting plastic compound integrates polypeptide/microorganism of the invention embedded in the mass of the compound.

Advantageously, such plastic compound can be used for the manufacturing plastic article wherein the polypeptide/microorganism of the invention is also included.

In a particular embodiment, the resulting plastic compound or plastic article is a biodegradable plastic compound or plastic article complying with at least one of the relevant standards and/or labels known by the person skilled in the art, such as standard EN 13432, standard ASTM D6400, OK Biodegradation Soil (Label Vinçotte), OK Biodegradation Water (Label Vinçotte), OK Compost (Label Vinçotte), OK Compost Home (Label Vinçotte).

A biodegradable plastic compound or plastic article refers to a plastic compound or plastic article that is at least partially transformed under environmental conditions into water, carbon dioxide or methane and biomass. As illustrated in the examples, preferred plastic compounds or plastic articles of the invention are biodegradable in water. Preferably, about 90% by weight of the plastic compound or plastic article is biodegraded in water within less than 90 days, more preferably within less than 60 days, even more preferably within less than 30 days. Alternatively or in addition, the plastic compound or plastic article may be biodegraded when exposed to wet and temperature conditions that occur in landscape. Preferably, about 90% by weight of the plastic compound or plastic article is biodegraded with less than 3 years in the environment, more preferably within less than 2 years, even more preferably within less than 1 year. Alternatively, the plastic compound or plastic article may be biodegraded under industrial composting conditions, wherein the temperature is maintained above 50° C.

Further aspects and advantages of the invention will be disclosed in the following examples, which should be considered as illustrative and do not limit the scope of this application.

EXAMPLES

Example 1: Purification and Identification of a Polyesterase from *Actinomadura keratinilytica* T16-1

*A. keratinilytica* NBRC 104111 strain T16-1 (Sukkum et al. 2009), isolated from Thai forest soils, was selected for the high PLA-degrading activity of its supernatant.

Enzyme Production in Fermentor

Batch experiment was performed in a 10-L fermentor (SARTORIUS Biostat Cplus). 500 mL of Yeast Malt Broth (YM, Sigma-Aldrich) pre-culture were used to inoculate 4.5 L of basal medium (gelatin 2.4 g/L; $(NH_4)_2SO_4$ 4 g/L; $MgSO_4.7H_2O$ 0.2 g/L; yeast extract 0.5 g/L; $K_2HPO_4$ 4 g/L; $KH_2PO_4$ 2 g/L adjusted at pH 6.8 with NaOH). The temperature was regulated at 46° C. and the pH maintained at 6.8 with the addition of a 10% (v/v) $H_3PO_4$ solution. The stirring rate was fixed at 70 rpm to enable a gentle mixing and the aeration rate (0.6 to 1.6 vvm) was regulated to provide the reactor with a dissolved oxygen level higher than 20% of air saturation, in order to avoid any oxygen limitation in the culture. The fermentor was connected to a computer and the MFCS/DA software carried out the on-line acquisition of the controlled parameters (pH, temperature, partial pressure of dissolved oxygen and $H_3PO_4$ addition) and allowed the monitoring and the regulation of these parameters on-line.

The culture duration was 50 hours. Supernatant, containing the extracellular enzyme, was recovered by centrifugation (13000 g-10 min) and conserved at 4° C.

Polyesterase Purification

The supernatant of the culture was concentrated 40 fold using Amicon Cell 500 mL (Merck Millipore) and a cellulose regenerated membrane with a pore size of 10 KDa (GE Healthcare Life Science). The resulting solution was dialyzed against 50 mM glycine-NaOH pH 10 buffer.

An AKTA Purifier apparatus (GE Healthcare Life Science) was used to carry out polypeptide purification, using an anion exchange purification HiTrap Q FF 1 mL column (GE Healthcare Life Science) with 50 mM glycine-NaOH pH 10 as loading buffer. Elution was carried out with a 0 to 1M NaCl gradient in 50 mM glycine-NaOH pH 10 buffer.

The presence of the polyesterase of the invention in the different fractions comprising the flow-through fraction was elucidated after TCA precipitation (v/v) by a stain-free SDS-PAGE gel (Bio-Rad) and by testing the capacity of the enzyme to produce a halo in a plate containing a mix of agarose (1%) and PLLA emulsion (0.5%, NaturePlast).

Determination of the Polypeptide N-Terminal Sequence

N-terminal sequencing of the polypeptide contained in the desired band was carried out, after passive extraction from gel, by the Edman microsequencing technique using a 494 microsequencer apparatus (Perkin Elmer Applied Biosystems) in the Pissaro platform of Rouen (France).

Molecular Biology Techniques

The general procedures used for DNA manipulation were previously described (Sambrook J, Russell D W. 2001. Molecular cloning: a laboratory manual, 3rd ed. Cold Spring Harbor Laboratory Press, Cold Spring Harbor, N.Y.) unless otherwise specified. Restriction enzymes and T4 DNA ligase were obtained from New England Biolabs and used according to the manufacturer's instructions. PCRs were performed using CloneAmp HiFi PCR Premix (Takara-Clontech). Synthetic oligonucleotides were synthesized by Eurogentec. PCR products were purified using the GenElute PCR Clean-Up Kit (Sigma-Aldrich). Plasmid DNA was introduced into *Escherichia coli* DH5α strain (Invitrogen) using the heat shock method. Plasmid DNA was obtained from *E. coli* using the QIAprep spin plasmid miniprep kit (Qiagen). Total RNA samples were obtained using the RNEASY Plus Mini Kit (Qiagen) and, subsequently, ribosomal RNAs were depleted using the RIBO-ZERO rRNA Removal Kit (Epicentre).

RNA Sequencing

Two RNA libraries, corresponding to the expression profiles of *A. keratinilytica* T16-1 in presence/absence of PLLA (NaturePlast, 500 µm), were constructed using the Illumina TruSeq Stranded mRNA kit and the ultra-high-throughput sequencing system Illumina HiSeq 2500. Paired-end reads (2×100 ob) were obtained using the chemistry v3 of the TruSeq SBS kit (Illumina).

Bioinformatic

Database searches were performed using the nonredundant sequence database accessible at the National Center for Biotechnology Information website (Worldwide Website: ncbi.nlm.nih.gov) using TBLASTN, BLASTX, and BLASTP (Altschul S F et al. 1997. Gapped BLAST and PSI-BLAST: a new generation of polypeptide database search programs. Nucleic Acids Res. 25:3389-3402). Sequence analysis was performed using Vector NTI software (Life Technologies), and multiple local alignments were carried out with ClustalW software (Thompson J D, Higgins D G, Gibson T J. 1994. CLUSTAL W: improving the sensitivity of progressive multiple sequence alignment through sequence weighting, position-specific gap penalties and weight matrix choice. Nucleic Acids. Res. 22:4673-4680).

Results

Polypeptide Purification

Polypeptide purification was realized using an anion exchange column at pH 10. Activity of the different fractions was tested on agarose plates containing PLA. Formation of a halo, indicating PLA hydrolysis, was only obtained with the flow-through fraction. A SDS-PAGE, with β-mercaptoethanol, demonstrated that the flow-through fraction contains a unique band (FIG. 1). This purification process enabled a pure polypeptide, presenting the activity of PLA hydrolysis to be obtained. The molecular weight of the polypeptide was evaluated to 27 kDa.

N-terminal sequencing of the mature protein contained in the band showed a unique 28 amino acid sequence:

```
                                       (SEQ ID NO: 3)
ATQNNPPSWGLDRIDQTNLPLSRSYTYN
```

The polypeptide purified in the flow-through showed a depolymerization activity on PLA powder. The specific activity of the polypeptide is 4.8 g of lactic acid produced per mg of enzyme and per hour (according to the protocol described below).

RNA sequencing results allowed to identify a DNA sequence, encoding for a polypeptide whose sequence showed a 100% identity with the 28 amino acids previously identified by N-terminal sequencing.

The DNA sequence determined is reproduced below (SEQ ID NO: 4), wherein the underlined sequence corresponds to the hypothetical peptide signal and propeptide:

```
                                              (SEQ ID NO: 4)
5'atgagacgacgtaccctgcccatcgccgtcctcgccgccgttccctg gccgtggcgggcgccctgcccgccggagccgccccgccgccccgcgt cccggtcgccatggcggccgccggacagggcgtcgccggacagtacatcg tgacgctgaagaagggcgtctcggtcgactcgaccgtcgccaagcgcgga atccgcacccagcaccgtttcggcaaggtgctgaacggcttctccgccaa gctcaccgatgaccaactgtccaagctgcgcaccacgccggtgtcgcgt ccatcgagcaggacgccgtcatcacggtggacgccacgcagaacaaccg ccgtcgtggggcctggaccgcatcgaccagacgaacctgccgctgtcgcg cagctacacctacaattccaccggcgcgggcgtgaacgcctacatcatcg acaccggcatctacaccgcgcactccgacttcggcggccgcgccaccaac gtctacgacgccctcggcggcaacggccaggactgcaacggccacggcac ccacgtcgcgggcaccgtcggcggcgccgcctacggcgtggccaaggcgg tcaacctgcgcggcgtgcgcgtgctcaactgcagcggcagcggcaccacc tccggtgtcatcgccggcatgaactgggtggccagcaaccacgtcaagcc cgccgtggcgaacatgtcgctgggcggcggctactcctcctccctgaaca cggccgccaacaacctggccagctccggcgtgttcctggccgtcgccgcg ggcaacgagaccaccaacgcctgcaaccgctcgccggccagcgccgccaa cgccaccacggtcgccgcgagcaccagcaccgacgcccgggcctcctaca gcaactacggctcgtgcgtccacctgtacgcgcccggctcgtccatcacc
```

-continued

```
tccgcctggctgaacggcggcaccaacaccatcagcggcacgtcgatggc cacgccgcacgtggccgggaccgccgccctctacaaggcgacctacggcg acgcctcgttcagcaccatccgcagctggctggtcagcaacgccacctcc ggcgtcatcaccggcaacgtgtcgggcaccccgaacctgctgctgaacaa gcgctccctgtaa 3'
```

The encoded polypeptide presents a sequence of 386 amino acids (SEQ ID NO: 5 below), wherein
  residues 1 to 29 correspond to the peptide signal,
  residues 30 to 110 correspond to the hypothetical propeptide and
  residues 111 to 386 correspond to the mature polypeptide.

```
SEQ ID NO: 5 (underlined propeptide sequence;
double underlined peptide signal):
MRRRTLPIAVLAAVPLAVAGALPAGAAPAAPAVPVAMAAAGQGVAGQYIV

TLKKGVSVDSTVAKRGIRTQHRFGKVLNGFSAKLTDDQLSKLRTTPGVAS

IEQDAVITVDATQNNPPSWGLDRIDQTNLPLSRSYTYNSTGAGVNAYIID

TGIYTAHSDFGGRATNVYDALGGNGQDCNGHGTHVAGTVGGAAYGVAKAV

NLRGVRVLNCSGSGTTSGVIAGMNWVASNHVKPAVANMSLGGGYSSSLNT

AANNLASSGVFLAVAAGNETTNACNRSPASAANATTVAASTSTDARASYS

NYGSCVHLYAPGSSITSAWLNGGTNTISGTSMATPHVAGTAALYKATYGD

ASFSTIRSWLVSNATSGVITGNVSGTPNLLLNKRSL

Mature polypeptide sequence (SEQ ID NO: 1):
ATQNNPPSWGLDRIDQTNLPLSRSYTYNSTGAGVNAYIIDTGIYTAHSDF

GGRATNVYDALGGNGQDCNGHGTHVAGTVGGAAYGVAKAVNLRGVRVLNC

SGSGTTSGVIAGMNWVASNHVKPAVANMSLGGGYSSSLNTAANNLASSGV

FLAVAAGNETTNACNRSPASAANATTVAASTSTDARASYSNYGSCVHLYA

PGSSITSAWLNGGTNTISGTSMATPHVAGTAALYKATYGDASFSTIRSWL

VSNATSGVITGNVSGTPNLLLNKRSL
```

The theoretical molecular weight calculated for this 276 amino acid mature polypeptide was 27.7 kDa, which corresponds to the molecular weight observed after purification of the polyesterase from supernatant of *A. keratinilytica* T16-1.

According to homology with known polypeptides, the polypeptide having polyesterase activity revealed the presence of two putative calcium binding sites, with residues Ala 172, Ala 174 and His 197 for the first one and residues Asp 12, Asp 15 and Gln 16 for the second one. The catalytic site of the polypeptide is composed by amino acids His 71, Asp 40 and Ser 221. In addition, two putative disulfide bonds have also been identified in the polypeptide sequence between the residues Cys 68-Cys 100 and Cys 164-Cys 195 (FIG. 2).

Example 2: Characterization of the Polyesterase from *A. keratinilytica* T16-1

The optimal pH and temperature of the enzyme were determined, and thermostability of the enzyme was studied.
Optimal pH and Temperature of the Polypeptide
The optimal pH of the enzyme is 8.5. Depolymerization tests in tubes magnetically stirred were performed at 50° C. in a range of pH between 7 and 9 with 600 µg of enzyme in 2 mL of buffer and 20 mg of Goodfellow PLA film. At pH 7, the enzyme shows few activity.

Depolymerization tests were carried out at 37° C., 45° C. and 50° C. at pH 8.5 with 600 µg of enzyme in 2 mL of buffer Tris-HCl pH 8.5 and 20 mg of Goodfellow PLA film. The optimal temperature of the enzyme is 50° C.
Polyesterase Thermostability
Polyesterase stability assays were realized in the temperature range from 4° C. to 60° C. Polyesterase is stable for months at 4° C. A compromise between stability and activity of the enzyme corresponds to a temperature of 45° C. At 45° C. the enzyme half-life time is 2.5 weeks. In addition, there is no loss of polyester degrading activity after a lyophilization procedure.

Example 3: Development of a PLA-Degradation Process

The aim of these experiments was to solve the problem of producing lactic acid in view of both potential inhibitor and drastically lowering pH during the reaction. The enzyme and the PLA were introduced and confined in a dialysis tube of 10 kDa. This tube is permeable to lactic acid and was placed in a volume of buffer, allowing to work at a constant pH and to dilute lactic acid thus limiting its potential inhibitory effect.
Enzymatic PLA Degradation
The degradation ability of the polypeptide of interest (SEQ ID NO: 1), was studied during hydrolysis kinetics of PLA. PLA conversion to lactic acid was followed by HPLC analysis.

The PLA degradation assays were carried out in a 10 kDa dialysis tube (cellulose membrane, width 25 mm, Sigma-Aldrich D9777-100FT). 90 µg of enzyme in 3 mL of Tris HCl 100 mM, pH 8.5 buffer, PLLA powder (Natureplast 500 µm), PLA films (Goodfellow, 50 µm thickness), or PLA objects were introduced and confined in the dialysis tube. The tube was placed in 50 mL (unless otherwise specified) of 100 mM Tris-HCl buffer in order to control the pH to 8.5. The buffer was supplemented with kanamycine (40 µg/mL) to avoid any contamination. The reaction was incubated at 45° C. under stirring (150 rpm). The objective of this procedure was to control the pH of the reaction and to avoid potential enzyme inhibition by lactic acid.

The degradation products (lactic acid and soluble oligomers) were quantified by HPLC analysis of the buffer outside the tubing (column Aminex HPX-87H (300 mm×7.8 mm), mobile phase $H_2SO_4$ 5 mM, temperature 50° C., flow rate 0.5 mL·min$^{-1}$, injected volume 20 µL). Standards of lactic acid (Sigma-Aldrich L1750-10G), dimer and trimer (homemade) were used for external calibration.

To quantify the interest of this process, PLA hydrolysis was realized with a dialysis system: in a tube magnetically stirred at 45° C. containing 50 mg of a PLA film (Goodfellow, 50 am thickness, 2% D-lactic acid), 90 µg of enzyme in 3 mL of Tris-HCl 100 mM pH8.5 buffer introduced in a tube. After 24 hours of reaction, 55% conversion was obtained in the proposed reactor.

Example 4: Evaluation of the Polyesterase Activity on PLA/PLLA of Different Granulometry The enzyme activity was evaluated during hydrolysis of PLA powders (PLLA NaturePlast, PLA Ingeo 7001D containing 4% D-lactic acid). Different particle sizes (100-250

μm, 250-500 μm, 500 μm-1 mm and 1-2 mm) were obtained by micronization and grinding of the commercial pellets (Table 1).

TABLE 1

Characteristics of PLA (Ingeo 7001D) and PLLA (Natureplast) powders: particle size and crystallinity.

|  | Particle size | Tg (° C.) | Crystallinity (%) |
|---|---|---|---|
| PLA Ingeo 7001D | 100-250 μm | 62 | 3 |
|  | 250-500 μm | 60 | 7 |
|  | 500 μm-1 mm | 63 | 41 |
|  | 1 mm-2 mm | 62 | 42 |
| PLLA Natureplast | 100-250 μm | 58 | 23 |
|  | 250-500 μm | 57 | 24 |
|  | 500 μm-1 mm | 59 | 34 |
|  | 1 mm-2 mm | 64 | 43 |

Differential Scanning Calorimetry (DSC) tests were used in order to determine glass temperature (Tg) and crystallinity of PLA, using a Q100 TA-RCS 90 Instrument under nitrogen atmosphere (50 mL/min) at a scanning rate of 10° C./min from −50° C. to 300° C. in aluminum pans on around 8 mg samples.

Hydrolysis performances of the two different PLA powders with the different particle sizes were determined in the reactor process described in example 3 with 100 mg of PLA powder, 60 μg of enzyme in 2 mL of Tris-HCl 100 mM pH8.5 buffer. Hydrolysis of PLA and PLLA powder of the same size were identical, indicating that the presence of 4% of D-lactic acid is not detrimental to hydrolysis performances. PLA crystallinity in the range 5 to 24% has low influence on hydrolysis performances. On the contrary, there is a strong influence of the particle size on hydrolysis rate of PLA and PLLA powders: thinnest the powders, more efficient the hydrolysis rate. It can be explained by an increase of the exchange surface between solid and liquid phases. (FIGS. 3 and 4).

A particle size in the range of 100-250 m enables 68% of conversion to be obtained in 24 hours.

If 10 mM of $CaCl_2$ is added in the reactor 95% of conversion of PLLA powder NaturePlast 500 lam was obtained after 80 hours of reaction.

Example 5: PLA Concentration Impact on the Enzyme Activity

The enzyme activity was evaluated during hydrolysis of PLLA powders at different concentrations (33 to 300 g/L) with the same protocol as described in example 3, 90 lag of enzyme in 3 mL of Tris-HCl 100 mM pH 8.5 buffer. The results are presented in Table 2.

Higher is the PLLA concentration, higher is the productivity of lactic acid formation tending to 0.2 g lactic acid/mg of enzyme/h with a concentration of 300 g/L of PLLA.

TABLE 2

Productivity obtained at 10 h of reaction during polyesterase-catalyzed hydrolysis of different PLLA concentrations.

| Productivity 10 h | PLLA 33 g/L | PLLA 100 g/L | PLLA 200 g/L | PLLA 300 g/L |
|---|---|---|---|---|
| $g_{Lactic\ acid}/mg_{enzyme}/h$ | 0.07 | 0.15 | 0.17 | 0.19 |
| Improvment factor | 1 | ×2.1 | ×2.3 | ×2.6 |

Example 6: Polyesterase-Catalyzed Hydrolysis of PLA Film into Lactic Acid

The same experimental protocol presented in example 3 was used during hydrolysis of PLA film (Goodfellow, 50 μm thickness, 2% D-lactic acid). The kinetic was carried out at 45° C. pH 8.5 with 90 μg of polyesterase in 3 mL of Tris-HCl 100 mM pH8.5 buffer and 50 mg of film (17 g/L).

Polyesterase is able to hydrolyze a film into lactic acid. 76% of conversion was obtained in 48 h, 82% in 72 h (FIG. 5).

Example 7: Polyesterase-Catalyzed Hydrolysis of PLA-Commercial Objects into Lactic Acid The same experimental protocol presented in example 3 was used during polyesterase-catalyzed hydrolysis of commercial objects (PLA cups, trays, film and cutlery). Hydrolysis tests were performed on powders (250-500 μm) of these objects. 100 mg of commercial object powders, 90 μg of enzyme in 3 mL of Tris-HCl 100 mM pH8.5 buffer were used.

The initial rate of hydrolysis is relatively similar whatever the PLA object (from 27% for the film to 44% for the cup at 10 hours). It is in the same range than the result obtained with PLLA NaturePlast powder (37%). However it is remarkable that a PLA cup is more easily converted in lactic acid than a PLLA powder. 98% of conversion of the PLA cup are obtained after 48 hours. 93% and 84% of conversion into lactic acid are obtained in 72 h for the film and the trays respectively. The cutlery is the object the most difficult to degrade, with a maximum of 60% of the object converted into lactic acid. It contains around 1% of $TiO_2$ and it was shown that the presence of $TiO_2$ is not responsible of this phenomenon.

Polyesterase is able to hydrolyze all the commercial objects into lactic acid (FIG. 6).

Example 8: Recycling Process Using the Enzyme of SEQ ID NO: 1

The aim of these experiments was to validate the industrial applicability of the PLA degrading solution of the invention, wherein the enzyme of SEQ ID NO: 1 and the PLA are introduced in a reactor without any dialysis system.

The PLA degradation assays were carried directly with the enzyme production medium obtained by fermentation as describe in Example 1. Supernatant, containing the extracellular enzyme, was recovered by centrifugation (13000 g-10 min) and conserved at 4° C.

400 mg of PLA Natureplast powder (Particle size<500 μm) were added directly to 25 ml of supernatant. 300 mg of Calcium carbonate and 100 mg of Calcium hydroxide were added in order to neutralize the lactic acid liberated during hydrolysis and to maintain the pH of the solution over 7. At the beginning of the reaction the pH was included between 9.0 and 9.8. The reaction mixture was incubated for 140 hours under agitation (300 rpm) at 45° C.

During the reaction, several samples of mixture were collected (1 ml) and filtered onto a 0.22 μm filter. 20 μl of filtrate were analyzed by HPLC to quantify the lactic acid and soluble oligomers (DP2) as described in Example 2. After 144 hours of reaction 17.5 g/l of lactic acid and 0.52 g/l of DP2 oligomer were obtained. The yield of conversion of PLA to lactic acid was greater than 77% (FIG. 7).

Example 9: Comparison of the PLA Degradation by Different Particular Polypeptides of the Invention The amino acid sequence of SEQ ID NO: 1 has been modified in order to improve its thermostability.

A first strategy was to introduce an additional disulphide bond in the structure of the polypeptide by performing two amino acid residue substitutions in the amino acid residue sequence of SEQ ID NO: 1 by introducing two cysteine residues at the residue positions 175 and 247 of SEQ ID NO: 1 (T175C and R247C).

A second strategy was to introduce extra salt bridges between amino acid residues 139 and 170 or between amino acid residues 143 and 173 of SEQ ID NO: 1. Accordingly, the first resulting variant contained the amino acid residues substitutions N139D and S170R, and the second resulting variant contained the amino acid residues substitutions N143R and N173E.

A third strategy was to perform site-directed mutagenesis on the nucleic sequence set forth in SEQ ID NO: 2 to produce 5 variants, each containing one amino acid residue substitution selected from S194P, H197D, L210P, G212N and I217K.

Additional variants of SEQ ID NO: 1, each containing an amino acid residues substitution selected from R166K, T160A, and L138A, have been tested and an activity comparable to the native polypeptide of SEQ ID NO: 1 has been measured.

Example 10: Recombinant Expression and Purification of a Polyesterase of SEQ ID NO: 1

Polyesterases of SEQ ID NO: 1 were expressed in three different hosts: *Yarrowia lipolytica*, *Bacillus subtilis*, and *E. coli*.

10A—Recombinant Expression of the Polyesterase in *Yarrowia lipolytica*

The polyesterase of SEQ ID NO: 1 was expressed in the yeast *Yarrowia lipolytica*, more precisely in the strain JMY1212, under the control of the constitutive promotor TEF, as previously described by Bordes et al., 2007 (F. Bordes, F. Fudalej, V. Dossat, J. M. Nicaud, et A. Marty (2007) A new recombinant protein expression system for high-throughput screening in the yeast *Yarrowia lipolytica*. J. of Mibrob. Meth., 70, 3, 493-502). The sequence corresponding to the propeptide followed by sequence of the gene expressing the mature polyesterase was optimised for the codon usage of *Yarrowia lipolytica*. This sequence was integrated downstream the secretion signal sequence of the gene coding for the lipase lip2 from *Y. lipolytica*.

The polyesterase was then successfully expressed in Erlenmeyer flasks (500 mL) containing medium $Y_1T_2O_3$ (50 mL total) made of yeast extract (10 g/L), bactotryptone (20 g/L), and glucose (30 g/L), buffered with phosphate buffer (100 mM, pH 6.8). Cells were incubated at 28° C. for 24 h until complete consumption of glucose. The cells were centrifuged at 10,000 rpm for 10 min, and supernatants were directly used in reactions.

The level of expression was similar to the one obtained in *A. keratinilytica* T16-1 but its thermostability was higher. Whereas the enzyme produced in *A. keratinilytica* T16-1 lost 78% of activity after 5 hours at 60° C., the enzyme expressed in *Y. lipolytica* is fully active after the same treatment.

10B—Recombinant Expression of the Polyesterase of SEQ ID NO: 1 in *Bacillus subtilis*

The polyesterase of SEQ ID NO: 1 was cloned and expressed in *Bacillus subtilis* as described in the commercial Takara kit. The sequence corresponding to the propeptide followed by sequence of the gene expressing the mature polyesterase was optimised for the codon usage of *Bacillus subtilis*. This sequence was integrated downstream a secretion signal sequence of *B. subtilis*.

The level of expression was similar to the one obtained in *A. keratinilytica* T16-1.

10C—Recombinant Expression of the Polyesterase of SEQ ID NO: 1 in *Escherichia Coli*

The polyesterase of SEQ ID NO: 1 was cloned and expressed in *E. coli*, and more precisely in BL21, *Origami* and *Rosetta* strains. The sequence corresponding to the propeptide followed by sequence of the gene expressing the mature polyesterase was optimised for the codon usage of *E. coli*. This sequence was integrated downstream either a PelB signal sequence for periplasm expression or the gene coding for the maltose binding protein, with or without an Histidine tag.

The level of expression was from two to three times higher than the one obtained in *A. keratinilytica* T16-1.

Using the Histidine tag, the protein was purified and tested for PLA depolymerisation using a 250-500 μm powder of PLA (Ingeo 7001D). The enzyme produced in *E. coli* presents the same specific activity than the enzyme expressed in *A. keratinilytica* T16-1.

Example 11: Production of a Biodegradable Plastic Compound Containing the Polypeptide of SEQ ID NO: 1

11A—Plastic Compound Production Process

A plastic compound is prepared, comprising PLA polymer (polylactic acid PLE 003 from Natureplast) in granulated form, that is previously dried at 65° C. for 4 hours, and a solid formulation of the polypeptide of SEQ ID NO: 1.

The polypeptide solid formulation is previously prepared according to the following steps: culturing a microorganism producing such polypeptide, filtration of such culture followed by ultrafiltration and diafiltration with a 3 kD membrane, addition of 10 g·l of maltodextrine and atomization of the mix in order to obtain the polypeptide under a dried powder form.

A compounding machine, or co-rotating twin-screw extruder, is used ("Coperion ZSK 18 megalab"). This compounding machine comprises successively a first feed element, two mixing elements, and a second feed element. The compounding machine comprises nine successive heating zones Z1 to Z9, wherein the temperature may be independently controlled and regulated. An additional zone Z10 is present after zone Z9, corresponding to the head of the twin-screw.

According to this experiment, 96% by weight of PLA is mixed with 4% by weight of liquid formulation of PLA depolymerase of SEQ ID NO: 1, and extruded, with the temperature profile described in table 3 below.

TABLE 3 temperature profile of the compounding machine

| | Zone | | | | | | | | | |
|---|---|---|---|---|---|---|---|---|---|---|
| | Z1 | Z2 | Z3 | Z4 | Z5 | Z6 | Z7 | Z8 | Z9 | Z10 (head) |
| T° C. | 135° C. | 150° C. | 170° C. | 180° C. | 140° C. | 140° C. | 140° C. | 140° C. | 140° C. | 140° C. |

The PLA is introduced in the principal hopper (before Z1 zone) with a flow of 9.6 kg/h. The PLA goes through zones Z1 to Z5, wherein the temperature was increased up to 180° C. (Z4) leading to molten PLA. The enzymes are then introduced with a flow of 0.4 kg/h, in Z6, through the side feeder NO: 2, where the temperature is decreased to 140° C.

Enzyme and PLA are then mixed together from zones Z7 to zone Z9, through the rotation of the twin-screw at 200 Rpm. The residence time from Z1 to Z9 is approximately 1 minute and 30 seconds. The mix of PLA and biological entities then arrive in the screw head (Z10) comprising two holes of a diameter of 2.5 mm, wherein the mix is pushed in order to form pellets, which are then cooled in water and dried before conditioning.

A plastic compound under granulated form is obtained, that contains 96% by weight of PLA, and 4% by weight of the formulation of PLA depolymerase of SEQ ID NO: 1. Such plastic compound may be used to produce plastic articles by any techniques well known per se in the art.

11B—Degradation Test of a Plastic Compound Comprising PLA and a Polypeptide of SEQ ID NO: 1.

Different comparative tests of biodegradability have been performed using:

- a plastic compound produced according to Example 11A, that contains 96% by weight of PLA, and 4% by weight of a formulation of PLA depolymerase of the invention
- a PLA compound produced as described in example 11A that contains 100% by weight of PLA (i.e., deprived of PLA depolymerase), referred as a control.

Such tests were performed at different temperatures: 28° C., 37° C. or 45° C.

Approximately 1 gram of PLA was put in 100 mL of Tris buffer (pH=9.5). The amount of PLA was accurately measured to assess the theoretical amount of lactic acid produced.

The biodegradability of the compound was assessed by the measurement of the conversion of PLA, more specifically the depolymerization of PLA into lactic acid or dimers of lactic acid. This conversion was followed by HPLC analysis.

The results (FIG. 8) showed that the PLA compound intergrating a PLA depolymerase shows a greater depolymerization rate (i.e., biodegradability) than the control PLA compound. The depolymerization of the PLA compound is even better at 37° C. or 45° C. than at 28° C.

The invention claimed is:

1. A polyester containing material comprising at least one polyester and a polypeptide comprising an amino acid sequence having at least 75% sequence identity to the full length amino acid sequence set forth in SEQ ID NO: 1 and having a polyester degrading activity.

2. The polyester containing material according to claim 1, wherein the polypeptide comprises an amino acid sequence having at least 94% sequence identity to the full length amino acid sequence set forth in SEQ ID NO: 1.

3. The polyester containing material of claim 1, wherein the at least one polyester is a synthetic polyester.

4. The polyester containing material of claim 1, wherein the at least one polyester is PLA.

5. The polyester containing material of claim 1, wherein the material is a plastic product.

6. The polyester containing material of claim 1, wherein the material is a plastic compound.

7. A process for preparing a polyester containing material according to claim 1, comprising a step of mixing the polyester with the polypeptide, wherein the mixing step is performed at a temperature at which the polyester is in a partially or totally molten state.

8. A process for preparing a polyester containing material according to claim 1, comprising a step of mixing the polyester with the polypeptide, wherein the polyester is PLA and wherein the mixing step is performed at a temperature at which PLA is in a partially or totally molten state.

9. A method for degrading a plastic product, wherein a plastic product comprising at least one polyester is contacted with a polypeptide comprising an amino acid sequence having at least 75% identity to the full length amino acid sequence set forth in SEQ ID NO: 1, and having a polyester degrading activity.

10. The method of claim 9, wherein the polyester is PLA and the polypeptide has a PLA degrading activity.

11. A method of producing monomers and/or oligomers from a polyester containing material, comprising exposing the polyester containing material to a polypeptide comprising an amino acid sequence having at least 75% identity to the full length amino acid sequence set forth in SEQ ID NO: 1, and having a polyester degrading activity, and recovering monomers and/or oligomers.

12. The method of claim 11, wherein the polyester is PLA and the polypeptide has a PLA degrading activity.

* * * * *

UNITED STATES PATENT AND TRADEMARK OFFICE
CERTIFICATE OF CORRECTION

| | |
|---|---|
| PATENT NO. | : 10,287,561 B2 |
| APPLICATION NO. | : 15/520431 |
| DATED | : May 14, 2019 |
| INVENTOR(S) | : Pablo Alvarez et al. |

Page 1 of 1

It is certified that error appears in the above-identified patent and that said Letters Patent is hereby corrected as shown below:

In the Specification

<u>Column 25,</u>
Line 43, "500 lam" should read --500 μm--.
Line 51, "90 lag" should read --90 μg--.

Signed and Sealed this
Twenty-fourth Day of September, 2019

Andrei Iancu
*Director of the United States Patent and Trademark Office*